US011987625B2

(12) United States Patent
Hart et al.

(10) Patent No.: US 11,987,625 B2
(45) Date of Patent: May 21, 2024

(54) ANTI-CD300F ANTIBODY AND USES THEREOF

(71) Applicant: DENDROCYTE BIOTECH PTY LTD, Balmain (AU)

(72) Inventors: Derek Nigel John Hart, New South Wales (AU); Georgina Jane Clark, New South Wales (AU); Robin Gasiorowski, New South Wales (AU)

(73) Assignee: DENDROCYTE BIOTECH PTY LTD, New South Wales (AU)

( * ) Notice: Subject to any disclaimer, the term of this patent is extended or adjusted under 35 U.S.C. 154(b) by 1309 days.

(21) Appl. No.: 16/462,688

(22) PCT Filed: Nov. 22, 2017

(86) PCT No.: PCT/AU2017/051288
§ 371 (c)(1),
(2) Date: May 21, 2019

(87) PCT Pub. No.: WO2018/094460
PCT Pub. Date: May 31, 2018

(65) Prior Publication Data
US 2023/0063312 A1 Mar. 2, 2023

(30) Foreign Application Priority Data
Nov. 22, 2016 (AU) .................... 2016904779

(51) Int. Cl.
*C07K 16/28* (2006.01)
*A61P 35/02* (2006.01)

(52) U.S. Cl.
CPC .......... *C07K 16/2803* (2013.01); *A61P 35/02* (2018.01); *C07K 2317/24* (2013.01); *C07K 2317/32* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 5,225,539 A | 7/1993 | Winter |
| 5,260,203 A | 11/1993 | Ladner et al. |
| 6,054,297 A | 4/2000 | Carter et al. |
| 7,270,969 B2 | 9/2007 | Watt et al. |
| 7,566,771 B1 | 7/2009 | Adair et al. |

FOREIGN PATENT DOCUMENTS

| WO | WO 2009/051957 | 4/2009 |
| WO | WO 2010/059821 | 5/2010 |
| WO | WO 2011/005715 | 1/2011 |
| WO | WO 2013/126746 | 8/2013 |
| WO | WO2017/135277 | * 8/2017 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Altschul et al., "Basic Local Alignment Search Tool", *J. Mol. Biol.* (1990) 215: 403-410.
Baines et al., "Purification of Immunoglobulin G (IgG)", *Methods in Molecular Biology*, (1992) vol. 10, pp. 79-104.
Chothia et al., "Canonical Structures for the Hypervariable Regions of Immunoglobulins", *J. Mol. Biol.* (1987), 196: 901-917.
Chothia et al., "Conformations of immunoglobulin hypervariable regions", *Nature* (1989) 342: 877-883.
Essono et al., "A general method allowing the design of oligonucleotide primers to amplify the variable regions from immunoglobulin cDNA", *J. Immunol Methods* (2003) 279: 251-266.
Francisco et al., "cAC10-vcMMAE, an anti-CD30-monomethyl auristatin E conjugate with potent and selective antitumor activity", *Blood* (2003) vol. 102, No. 4, pp. 1458-1465.
Gamis et al., "Gemtuzumab Ozogamicin in Children and Adolescents With De Novo Acute Myeloid Leukemia Improves Event-Free Survival by Reducing Relapse Risk: Results From the Randomized Phase III Children's Oncology Group Trial AAML0531", *J. Clin. Oncol.* (2014); 32(27):3021-32 plus 8 page Appendix.
Graf et al., "Codon-Optimized Genes that Enable Increased Heterologous Expression in Mammalian Cells and Elicit Efficient Immune Responses in Mice after Vaccination of Naked DNA", *Methods Mol. Med.* (2004) vol. 94, pp. 197-210.
Hills et al., "The Addition of Gemtuzumab Ozogamicin to Induction Chemotherapy in Acute Myeloid Leukaemia: An Individual Patent Data Meta-analysis of Randomised Trials in Adults", *The Lancet Oncology* (2014) 15(9):986-96.
Honegger et al., "Yet Another Numbering Scheme for Immunoglobulin Variable Domains: An Automatic Modeling and Analysis Tool", *J. Mol. Biol.* (2001) 309: 657-670.
Krebber et al., "Reliable cloning of functional antibody variable domains from hybridomas and spleen cell repertoires employing a reengineered phage display system", *J. Immunol Methods* (1997) 201: 35-55.

(Continued)

*Primary Examiner* — Meera Natarajan
(74) *Attorney, Agent, or Firm* — FINNEGAN, HENDERSON, FARABOW, GARRETT & DUNNER, LLP

(57) ABSTRACT

The present disclosure relates to an isolated antibody, or antigen binding fragment thereof, which specifically binds to an extracellular domain of cd300f, wherein the antibody, or antigen binding fragment thereof, comprises a heavy chain variable region which comprises: (a) an amino acid sequence that is at least 70% identical to the amino acid sequence represented by seq id no: 1; and/or (b) a complementarity determining region 1 (cdr1) that comprises the amino acid sequence represented by seq id no: 2, a complementarity determining region 2 (cdr2) that comprises an amino acid sequence that is represented by seq id no: 3, and/or a complementarity determining region 3 (cdr3) that comprises an amino acid sequence that is represented by seq id no: 4, compositions comprising the antibody, antigen binding fragment thereof, and uses for therapy.

13 Claims, 13 Drawing Sheets
Specification includes a Sequence Listing.

(56) References Cited

OTHER PUBLICATIONS

Laszlo et al., "Cellular determinants for preclinical activity of a novel CD33/CD3 bispecific T-cell engager (BiTE) antibody, AMG 330, against human AML", *Blood* (2014) 123(4): 554-561.
Lipman et al., "Rapid and Sensitive Protein Similarity Searches", *Science* (1985) 227(4693): 1435-1441.
Loffler et al., "A recombinant bispecific single-chain antibody, CD19 X CD3, induces rapid and high lymphoma-directed cytotoxicity by unstimulated T lymphocytes", *Blood* (2000) 95: 2098-2103.
O'Hear et al., "Anti-CD33 chimeric antigen receptor targeting of acute myeloid leukemia", *Haematologica* (2015) 100(3): 336-344.
Raab et al., "The GeneOptimizer Algorithm: using a sliding window approach to cope with the vast sequence space in multiparameter DNA sequence optimization", *Systems and Synthetic Biology* (2010) 4(3): 215-225.
Maude et al., "CD19-targeted chimeric antigen receptor T-cell therapy for acute lymphoblastic leukemia", *Blood* (2015) vol. 125, No. 26, pp. 4017-4023.
Wayne et al., "Antibody Derivatives as New Therapeutics for Hematologic Malignancies", *Blood* (2014) 123(16): 2470-2477.
Gasiorowski, R.E. et al., "Antibody therapy for acute myeloid leukemia," British Journal of Haematology, vol. 164, No. 4, pp. 481-495, published online Dec. 10, 2013.
Korver, W. et al., "Monoclonal antibodies against IREM-1: potential for targeted therapy of AML," Leukemia (2009), vol. 23, pp. 1587-1597.

\* cited by examiner

Figure 9

A. Run data

| Index | Show | Analyze | Ref. | Sample ID | Conc. (nM) | Run time (s) | Shaker speed (rpm) | Integration (ms) | Biosensor Type | Information | Status |
|---|---|---|---|---|---|---|---|---|---|---|---|
| 1 | 1 | 1 | 0 | | 8.333 | 510 | 2200 | 1.8 | AHC | | |
| 3 | 1 | 1 | 0 | | 33.33 | 510 | 2200 | 1.8 | AHC | | |
| 2 | 1 | 1 | 0 | | 16.67 | 510 | 2200 | 1.8 | AHC | | |
| 4 | 1 | 1 | 0 | | 66.67 | 510 | 2200 | 1.8 | AHC | | |
| 5 | 1 | 1 | 0 | | 0 | 510 | 2200 | 1.8 | AHC | | |

B. Analysis data

| Index | Sample ID | Conc. (nM) | Information | KD (M) | Ka (1/Ms) | Ka Error | Kd (1/s) | Kd Error | Rmax | Rmax Error | R equilibrium |
|---|---|---|---|---|---|---|---|---|---|---|---|
| 1 | | 8.333 | | 3.656e-10 | 5.144e5 | 7.087e3 | 1.881e-4 | 3.58e-5 | 0.4634 | 0.01163 | 0.4439 |
| 2 | | 16.67 | | 3.656e-10 | 5.144e5 | 7.087e3 | 1.881e-4 | 3.58e-5 | 0.3171 | 0.004432 | 0.3103 |
| 3 | | 33.33 | | 3.656e-10 | 5.144e5 | 7.087e3 | 1.881e-4 | 3.58e-5 | 0.3016 | 0.002393 | 0.2983 |
| 4 | | 66.67 | | 3.656e-10 | 5.144e5 | 7.087e3 | 1.881e-4 | 3.58e-5 | 0.2739 | 0.001154 | 0.2724 |
| 5 | | 0 | | | | | | | | | |

Figure 12

```
                         CDR1                                    CDR2
A: MESGGGLVQP GGPLKLSCAA SGFGFSGSWM SWVRQAPGKG LEWIGQ INPD SSTINYTPSL
B: MESGGGLVQP GGSLRLSCAA SGFGFSGSWM SWVRQAPGKG LEWVAN INPD SSTINYVDSV
                                          CDR3
A: KDKFTISRDN AKNTLYLQIN KVRSEDTALY YCARRGFFEG YSAWFAYW
B: KGRFTISRDN AKNSLYLQMS KVRSEDTALY YCARRGFFEG YSAWFAYW
```

SEQUENCE LISTING

<160> NUMBER OF SEQ ID NOS: 40

<210> SEQ ID NO 1
<211> LENGTH: 108
<212> TYPE: PRT
<213> ORGANISM: Artificial Sequence
<220> FEATURE:
<223> OTHER INFORMATION: DCR-2 VH region

<400> SEQUENCE: 1

Met Glu Ser Gly Gly Gly Leu Val Gln Pro Gly Gly Pro Leu Lys Leu
1               5                   10                  15

Ser Cys Ala Ala Ser Gly Phe Gly Phe Ser Gly Ser Trp Met Ser Trp
                20                  25                  30

Val Arg Gln Ala Pro Gly Lys Gly Leu Glu Trp Ile Gly Gln Ile Asn
            35                  40                  45

Pro Asp Ser Ser Thr Ile Asn Tyr Thr Pro Ser Leu Lys Asp Lys Phe
        50                  55                  60

Ile Ile Ser Arg Asp Asn Ala Lys Asn Thr Leu Tyr Leu Gln Ile Asn
65                  70                  75                  80

Lys Val Arg Ser Glu Asp Thr Ala Leu Tyr Tyr Cys Ala Arg Arg Gly
                85                  90                  95

Phe Phe Glu Gly Tyr Ser Ala Trp Phe Ala Tyr Trp
            100                 105

<210> SEQ ID NO 2
<211> LENGTH: 8
<212> TYPE: PRT
<213> ORGANISM: Artificial Sequence
<220> FEATURE:
<223> OTHER INFORMATION: CDR1 of VH of DCR-2

<400> SEQUENCE: 2

Gly Phe Gly Phe Ser Gly Ser Trp
1               5

<210> SEQ ID NO 3
<211> LENGTH: 8
<212> TYPE: PRT
<213> ORGANISM: Artificial Sequence
<220> FEATURE:
<223> OTHER INFORMATION: CDR2 of VH of DCR-2

<400> SEQUENCE: 3

Ile Asn Pro Asp Ser Ser Thr Ile
1               5

<210> SEQ ID NO 4
<211> LENGTH: 15
<212> TYPE: PRT
<213> ORGANISM: Artificial Sequence
<220> FEATURE:
<223> OTHER INFORMATION: CDR3 of VH of DCR-2

<400> SEQUENCE: 4

Ala Arg Arg Gly Phe Phe Glu Gly Tyr Ser Ala Trp Phe Ala Tyr
1               5                   10                  15

<210> SEQ ID NO 5
<211> LENGTH: 100
<212> TYPE: PRT
<213> ORGANISM: Artificial Sequence
<220> FEATURE:
<223> OTHER INFORMATION: VL of DCR-2

-continued

<400> SEQUENCE: 5

Ile Leu Met Thr Gln Thr Pro Lys Phe Leu Leu Val Ser Ala Gly Asp
1               5                   10                  15

Arg Val Thr Ile Thr Cys Lys Ala Ser Gln Ser Val Ser Asn Asp Val
            20                  25                  30

Ala Trp Tyr Gln Gln Lys Pro Gly Gln Ser Pro Ser Leu Leu Ile Tyr
        35                  40                  45

Tyr Ala Ser Asn Arg Asn Thr Gly Val Pro Asp Arg Phe Thr Gly Ser
    50                  55                  60

Gly Tyr Glu Thr Asp Phe Thr Phe Thr Ile Ser Thr Val Gln Ala Glu
65                  70                  75                  80

Asp Leu Ala Val Tyr Phe Cys Gln Gln Asp Tyr Thr Ser Pro Trp Thr
                85                  90                  95

Phe Gly Gly Gly
            100

<210> SEQ ID NO 6
<211> LENGTH: 6
<212> TYPE: PRT
<213> ORGANISM: Artificial Sequence
<220> FEATURE:
<223> OTHER INFORMATION: CDR1 of VL of DCR-2

<400> SEQUENCE: 6

Gln Ser Val Ser Asn Asp
1               5

<210> SEQ ID NO 7
<211> LENGTH: 3
<212> TYPE: PRT
<213> ORGANISM: Artificial Sequence
<220> FEATURE:
<223> OTHER INFORMATION: CDR2 of VL of DCR-2

<400> SEQUENCE: 7

Tyr Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: DCR3 of VL of DCR-2

<400> SEQUENCE: 8

Gln Gln Asp Tyr Thr Ser Pro Trp Thr
1               5

<210> SEQ ID NO 9
<211> LENGTH: 324
<212> TYPE: DNA
<213> ORGANISM: Artificial Sequence
<220> FEATURE:
<223> OTHER INFORMATION: VH region of DCR2

<400> SEQUENCE: 9
atggagtctg gaggtggcct ggtgcagcct ggaggacccc tgaaactctc ctgtgcagcc      60
tcaggattcg gttttagtgg atcttggatg agttgggtcc ggcaggctcc agggaaaggg     120
ctagaatgga ttggacaaat taatccagat agcagtacga taaattatac accatctcta     180

```
aaggataaat tcatcatctc cagagacaac gccaaaaata ccctgtacct gcaaattaac    240
aaagtgagat ctgaggacac agcccttat tactgtgcaa gacggggtt ctttgaaggt      300 tactccgcct ggtttgctta ctgg                                           324
```

<210> SEQ ID NO 10
<211> LENGTH: 300
<212> TYPE: DNA
<213> ORGANISM: Artificial Sequence
<220> FEATURE:
<223> OTHER INFORMATION: VL region of DCR2

<400> SEQUENCE: 10

```
attttgatga cccagactcc caaattcctg cttgtatcag caggagacag ggtgaccata    60
acctgcaagg ccagtcagag tgtgagtaat gatgtagctt ggtaccaaca gaagccaggg    120
cagtctcctt cactcctgat atactatgca tccaatcgca acactggagt ccctgatcgc    180
ttcactggca gtggatatga cggatttc acttcacca tcagcactgt gcaggctgaa       240
gacctggcag tttatttctg tcagcaggat tatacctctc cgtggacgtt cggtggaggc    300
```

<210> SEQ ID NO 11
<211> LENGTH: 1422
<212> TYPE: DNA
<213> ORGANISM: Artificial Sequence
<220> FEATURE:
<223> OTHER INFORMATION: codon optimised chimeric heavy chain

<400> SEQUENCE: 11

```
atggtcctga gctgctgta cctgctgaca gctctgcctg catcctgtc tgaggtccag      60 ctgcaagagt ctggccccat ggaatctggc ggaggattgg ttcaacctgg cggccctctg    120
aagctgtctt gtgccgcttc tggcttcggc ttctccggct cttggatgtc ctgggtccga    180
caggctcctg gcaaaggcct ggaatggatc ggccagatca ccccgactc ctccaccatc    240 aactacaccc ctagcctgaa ggacaagttc atcatctccc gggacaacgc caagaacacc    300
ctgtacttgc agatcaacaa agtgcggagc gaggacaccg ctctgtacta ctgtgccaga    360
cggggcttct tcgagggcta ctctgcttgg tttgcctact ggggccaggg cacactggtc    420
acagtttctg ccgcctctac caagggaccc agcgttttcc ctctggctcc atcctccaag    480
tctacctctg gcgaacagc tgctctgggc tgcctggtca aggactactt tcctgagcca    540
gtgaccgtgt cctggaactc tggcgctctg acatctggcg tgcacacctt ccagctgtg    600 ctgcagtcct ccgcctgta ctctctgtcc tctgtcgtga ccgtgccttc agctctctg    660 ggaacccaga cctacatctg caatgtgaac cacaagcctt ccaacaccaa ggtggacaag    720
aaggtggaac ccagtcctg cgacaagacc cacacctgtc ctccatgtcc tgctccagaa    780
ctgctcggcg gaccttccgt gttcctgttt cctccaaagc ctaaggacac cctgatgatc    840
tctcggaccc ctgaagtgac ctgcgtggtg gtggatgtgt ccacgagga tcccgaagtg    900 aagttcaatt ggtacgtgga cggcgtggaa gtgcacaatg ccaagaccaa gcctagagag    960
gaacagtaca actccaccta tagagtggtg tccgtgctga ccgtgctgca ccaggattgg   1020
ctgaacggca agagtacaa gtgcaaggtc tccaacaagg cctgcctgc tcctatcgaa    1080 aagaccatct ccaaggccaa gggccagcct agggaacccc aggtttacac cttgcctcca   1140
tctcgggacg agctgaccaa gaaccaggtg tccctgacct gtctcgtgaa gggcttctac   1200
ccctccgata tcgccgtgga atgggagtct aatggccagc tgagaacaa ctacaagaca    1260 acccctcctg tgctggactc cgacggctca ttcttcctgt actccaagct gacagtggac   1320
```

```
aagtccagat ggcagcaggg caacgtgttc cctgctccg tgatgcacga ggccctgcac    1380
aatcactaca cccagaagtc cctgtctctg tccctggca ag                       1422
```

<210> SEQ ID NO 12
<211> LENGTH: 702
<212> TYPE: DNA
<213> ORGANISM: Artificial Sequence
<220> FEATURE:
<223> OTHER INFORMATION: codon optimised chimeric light chain

<400> SEQUENCE: 12

```
atggactctc aggcccaggt gctgatgctg ctgctgttgt gggtgtccgg cacctgtggc     60
gacatcctga tgacccagac tcctaagttc ctgctggtgt ctgccggcga cagagtgacc    120
atcacatgca aggcctctca gtccgtgtcc aacgacgtgg cctggtatca gcagaagcct    180
ggccagtctc ctagcctgct gatctactac gcctccaaca gaaacaccgg cgtgcccgat    240
agattcaccg gctctggcta cgagacagac ttcaccttca ccatctccac cgtgcaggcc    300
gaggatctgg ccgtgtactt ctgccagcaa gactacacct ctccatggac ctttggcgga    360
ggcaccaagc tggaaatcaa gcggacagtg gccgctcctt ccgtgttcat cttcccacct    420
tccgacgagc agctgaagtc tggcacagcc tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac agcacctaca gcctgtcctc cacactgacc    600
ctgtccaagg ccgactacga gaagcacaag gtgtacgcct gcgaagtgac ccatcagggc    660
ctgtctagcc ctgtgaccaa gtctttcaac cggggcgagt gc                      702
```

<210> SEQ ID NO 13
<211> LENGTH: 474
<212> TYPE: PRT
<213> ORGANISM: Artificial Sequence
<220> FEATURE:
<223> OTHER INFORMATION: heavy chain encoded by optimised nucleotide
      sequence

<400> SEQUENCE: 13

```
Met Val Leu Ser Leu Leu Tyr Leu Leu Thr Ala Leu Pro Gly Ile Leu
1               5                   10                  15

Ser Glu Val Gln Leu Gln Glu Ser Gly Pro Met Glu Ser Gly Gly Gly
            20                  25                  30

Leu Val Gln Pro Gly Gly Pro Leu Lys Leu Ser Cys Ala Ala Ser Gly
        35                  40                  45

Phe Gly Phe Ser Gly Ser Trp Met Ser Trp Val Arg Gln Ala Pro Gly
    50                  55                  60

Lys Gly Leu Glu Trp Ile Gly Gln Ile Asn Pro Asp Ser Ser Thr Ile
65                  70                  75                  80

Asn Tyr Thr Pro Ser Leu Lys Asp Lys Phe Ile Ile Ser Arg Asp Asn
                85                  90                  95

Ala Lys Asn Thr Leu Tyr Leu Gln Ile Asn Lys Val Arg Ser Glu Asp
            100                 105                 110

Thr Ala Leu Tyr Tyr Cys Ala Arg Arg Gly Phe Phe Glu Gly Tyr Ser
        115                 120                 125

Ala Trp Phe Ala Tyr Trp Gly Gln Gly Thr Leu Val Thr Val Ser Ala
    130                 135                 140

Ala Ser Thr Lys Gly Pro Ser Val Phe Pro Leu Ala Pro Ser Ser Lys
145                 150                 155                 160
```

Ser Thr Ser Gly Gly Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 14
<211> LENGTH: 234
<212> TYPE: PRT
<213> ORGANISM: Artificial Sequence
<220> FEATURE:
<223> OTHER INFORMATION: light chain encoded by codon optimised
      nucleotide sequence

<400> SEQUENCE: 14

Met Asp Ser Gln Ala Gln Val Leu Met Leu Leu Leu Leu Trp Val Ser
1               5                   10                  15

Gly Thr Cys Gly Asp Ile Leu Met Thr Gln Thr Pro Lys Phe Leu Leu
            20                  25                  30

Val Ser Ala Gly Asp Arg Val Thr Ile Thr Cys Lys Ala Ser Gln Ser

```
                35                  40                  45
Val Ser Asn Asp Val Ala Trp Tyr Gln Gln Lys Pro Gly Gln Ser Pro
 50                  55                  60

Ser Leu Leu Ile Tyr Tyr Ala Ser Asn Arg Asn Thr Gly Val Pro Asp
 65                  70                  75                  80

Arg Phe Thr Gly Ser Gly Tyr Glu Thr Asp Phe Thr Phe Thr Ile Ser
                 85                  90                  95

Thr Val Gln Ala Glu Asp Leu Ala Val Tyr Phe Cys Gln Gln Asp Tyr
                100                 105                 110

Thr Ser Pro Trp Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 15
<211> LENGTH: 108
<212> TYPE: PRT
<213> ORGANISM: Artificial Sequence
<220> FEATURE:
<223> OTHER INFORMATION: humanised VH of DCR-2

<400> SEQUENCE: 15

Met Glu Ser Gly Gly Gly Leu Val Gln Pro Gly Gly Ser Leu Arg Leu
  1               5                  10                  15

Ser Cys Ala Ala Ser Gly Phe Gly Phe Ser Gly Ser Trp Met Ser Trp
                 20                  25                  30

Val Arg Gln Ala Pro Gly Lys Gly Leu Glu Trp Val Ala Asn Ile Asn
                 35                  40                  45

Pro Asp Ser Ser Thr Ile Asn Tyr Val Asp Ser Val Lys Gly Arg Phe
 50                  55                  60

Thr Ile Ser Arg Asp Asn Ala Lys Asn Ser Leu Tyr Leu Gln Met Ser
 65                  70                  75                  80

Lys Val Arg Ser Glu Asp Thr Ala Leu Tyr Tyr Cys Ala Arg Arg Gly
                 85                  90                  95

Phe Phe Glu Gly Tyr Ser Ala Trp Phe Ala Tyr Trp
                100                 105

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
```

```
tacctgctcc tcttctg                                                   17

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
ccaagccatt cactgtt                                                   17

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
tctcaggcta ctccattgtc actca                                          25

<210> SEQ ID NO 19
<211> LENGTH: 16
<212> TYPE: DNA
<213> ORGANISM: Artificial Sequence
<220> FEATURE:
<223> OTHER INFORMATION: Primer

<400> SEQUENCE: 19
cttgggtgct gaggat                                                    16

<210> SEQ ID NO 20
<211> LENGTH: 16
<212> TYPE: DNA
<213> ORGANISM: Artificial Sequence
<220> FEATURE:
<223> OTHER INFORMATION: Primer

<400> SEQUENCE: 20
aggtggctac tgaggt                                                    16

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
caggaaccga cctactgcaa catg                                           24

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
caccagtcac ccaagaagaa actag                                          25

<210> SEQ ID NO 23
<211> LENGTH: 19
<212> TYPE: DNA
<213> ORGANISM: Artificial Sequence
```

```
<220> FEATURE:
<223> OTHER INFORMATION: Primer

<400> SEQUENCE: 23
catcccggct gctgttgtc                                              19

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ccaactctga ccggccacca                                             20

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
gtggccgcct cactcttg                                               18

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
gggtcaggtc tgcatagca                                              19

<210> SEQ ID NO 27
<211> LENGTH: 26
<212> TYPE: DNA
<213> ORGANISM: Artificial Sequence
<220> FEATURE:
<223> OTHER INFORMATION: Primers

<400> SEQUENCE: 27
ttggaggatg atgaagtacc agcaga                                      26

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gtcacccaag aagaaactag ca                                          22

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ggaaccctca ctcctgttgt c                                           21
```

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ccaactctga ccggccacca                                          20

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
gcctctccac agccatctg                                           19

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
ggagtagcct tgactcttag ca                                       22

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
atgtggctgc ctcagctcga cct                                      23

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tgaagagaat ccacaaggaa ttga                                     24

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
caacaggacc tgctgaacac tg                                       22

<210> SEQ ID NO 36
<211> LENGTH: 22
<212> TYPE: DNA
<213> ORGANISM: Artificial Sequence
<220> FEATURE:
<223> OTHER INFORMATION: Primer

```
<400> SEQUENCE: 36
tgatctggca cgggaccctc ca                                              22

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
gcagaagctt gggtacctgt agtttgttcc                                      30

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
tatctcgaga ttctagaagg cctgctgtag gt                                   32

<210> SEQ ID NO 39
<211> LENGTH: 19
<212> TYPE: PRT
<213> ORGANISM: Artificial Sequence
<220> FEATURE:
<223> OTHER INFORMATION: Peptide

<400> SEQUENCE: 39

Glu Val Lys Leu Val Glu Ser Gly Gly Gly Leu Val Gln Pro Gly Gly
1               5                   10                  15

Ser Leu Arg

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
gaggtgaagc tgrtggartc tgg                                             23
```

US 11,987,625 B2

ANTI-CD300F ANTIBODY AND USES THEREOF

REFERENCE TO SEQUENCE LISTING SUBMITTED ELECTRONICALLY

An official replacement copy of the sequence listing is submitted electronically via EFS-WEB as an ASCII formatted sequence listing with a file named Replacement Sequence listing.txt, having a file size of 19 KB. The sequence listing contained in this ASCII formatted document is part of the specification and is herein incorporated by reference in its entirety.

TECHNICAL FIELD

The present disclosure relates to an antibody, or antigen binding fragment thereof, that specifically binds to a CD300f polypeptide, and to the use of that antibody, or antigen binding fragment thereof, in therapy.

BACKGROUND

Myeloid leukaemias, such as AML, are a cancer of the myeloid line of blood cells. AML is characterized by rapid growth of abnormal white blood cells that accumulate in the bone marrow and interfere with production of normal blood cells. AML is the most common acute leukemia affecting adults, and the incidence of the AML increases with age. As a consequence, AML is expected to increase in incidence as the population ages.

Despite major advances in understanding the pathogenesis of myeloid leukaemias such as AML, patient outcomes remain unsatisfactory. The main treatment for AML is chemotherapy. A significant proportion of younger patients may be cured with intensive chemotherapy with or without allogeneic bone marrow transplant. However these therapies are not suitable for older patients who constitute the majority of those diagnosed with AML. Antibody therapy has also been trialed for treatment of AML. In this regard, the CD33 immunoconjugate gemtuzumab ozogamicin (GO) was trialed but withdrawn in 2010 following disappointing results in a phase III study. However follow up studies showed in combination therapy GO improved overall survival in some patients (Gamis A S, et al. J Clin Oncol. 2014; 32(27):3021-32.; Hills R K, et al. The Lancet Oncology. 2014; 15(9): 986-96).

Other targets in addition to CD33, which have been identified as potential targets by a variety of proteomics and transcriptomics of myeloid cell lines and some AML samples include CD123, CD96, CD44, CD47, CD32, CLL-1, IRAP and TIM-3. These molecules are all expressed to a greater or lesser degree by normal cells of the myeloid lineage and a number are also expressed on healthy bone marrow HSC raising the possibility of haematological toxicity.

What are needed are alternative molecules which bind targets on acute myeloid leukemia cells and/or their precursors for treatment of myeloid leukaemias, such as AML.

SUMMARY

CD300f is a member of the CD300f family of immunoregulatory molecules encoded by a gene complex on chromosome 17q25. It is a transmembrane glycoprotein with a cytoplasmic region and an extracellular domain. The cytoplasmic region contains both inhibitory ITIMs and PI3K phosphorylation sites. CD300f is upregulated in AML samples. CD300f is therefore a target for treatment of conditions associated with expression of CD300f, such as AML.

The inventors have produced a monoclonal antibody, referred to herein as DCR-2, which specifically binds to the extracellular domain of CD300f.

A first aspect provides an isolated antibody, or antigen binding fragment thereof, which specifically binds to an extracellular domain of CD300f, wherein the antibody, or antigen binding fragment thereof, comprises a heavy chain variable region which comprises:
  (a) an amino acid sequence that is at least 70% identical to the amino acid sequence represented by SEQ ID NO: 1; and/or
  (b) a complementarity determining region 1 (CDR1) that comprises the amino acid sequence represented by SEQ ID NO: 2, a complementarity determining region 2 (CDR2) that comprises an amino acid sequence that is represented by SEQ ID NO: 3, and/or a complementarity determining region 3 (CDR3) that comprises an amino acid sequence that is represented by SEQ ID NO: 4.

A second aspect provides an isolated antibody, or antigen binding fragment thereof, which specifically binds to an extracellular domain of CD300f, wherein the antibody, or antigen binding fragment thereof, comprises a light chain variable region which comprises:
  (a) an amino acid sequence that is at least 70% identical to the amino acid sequence represented by SEQ ID NO: 5; and/or
  (b) a complementarity determining region 1 (CDR1) that comprises an amino acid sequence represented by SEQ ID NO: 6, a complementarity determining region 2 (CDR2) that comprises an amino acid sequence represented by SEQ ID NO: 7, and/or a complementarity determining region 3 (CDR3) that comprises an amino acid sequence represented by SEQ ID NO: 8.

A third aspect provides an isolated antibody, or antigen binding fragment thereof, which specifically binds to an extracellular domain of CD300f, wherein the antibody, or antigen binding fragment thereof, comprises:
  (a) a heavy chain variable region which comprises:
    (i) an amino acid sequence that is at least 70% identical to the amino acid sequence of the amino acid sequence represented by SEQ ID NO: 1; and/or
    (ii) a complementarity determining region 1 (CDR1) that comprises the amino acid sequence represented by SEQ ID NO: 2, a complementarity determining region 2 (CDR2) that comprises an amino acid sequence that is represented by SEQ ID NO: 3, and/or a complementarity determining region 3 (CDR3) that comprises an amino acid sequence that is represented by SEQ ID NO: 4; and
  (b) a light chain variable region which comprises:
    (i) an amino acid sequence that is at least 70% identical to the amino acid sequence represented by SEQ ID NO: 5; and/or
    (ii) a complementarity determining region 1 (CDR1) that comprises an amino acid sequence represented by SEQ ID NO: 6, a complementarity determining region 2 (CDR2) that comprises an amino acid sequence represented by SEQ ID NO: 7, and/or a complementarity determining region 3 (CDR3) that comprises an amino acid sequence represented by SEQ ID NO: 8.

A fourth aspect provides an isolated antibody, or antigen binding fragment thereof, which specifically binds to an extracellular domain of CD300f, wherein the antibody, or antigen binding fragment thereof, comprises:
- (a) a heavy chain variable region which comprises a complementarity determining region 1 (CDR1) that comprises the amino acid sequence represented by SEQ ID NO: 2, a complementarity determining region 2 (CDR2) that comprises an amino acid sequence that is represented by SEQ ID NO: 3, and a complementarity determining region 3 (CDR3) that comprises an amino acid sequence that is represented by SEQ ID NO: 4; and
- (b) a light chain variable region which comprises a complementarity determining region 1 (CDR1) that comprises an amino acid sequence represented by SEQ ID NO: 6, a complementarity determining region 2 (CDR2) that comprises an amino acid sequence represented by SEQ ID NO: 7, and a complementarity determining region 3 (CDR3) that comprises an amino acid sequence represented by SEQ ID NO: 8.

A fifth aspect provides an isolated antibody, or antigen binding fragment thereof, which specifically binds to an extracellular domain of CD300f, wherein the antibody, or antigen binding fragment thereof, comprises a heavy chain variable region which comprises the amino acid sequence represented by SEQ ID NO: 1, or a light chain variable region which comprises the amino acid sequence represented by SEQ ID NO: 5.

A sixth aspect provides an isolated antibody, or antigen binding fragment thereof, which specifically binds to an extracellular domain of CD300f, wherein the antibody, or antigen binding fragment thereof, comprises a heavy chain variable region which comprises the amino acid sequence represented by SEQ ID NO: 1, and a light chain variable region which comprises the amino acid sequence represented by SEQ ID NO: 5.

A seventh aspect provides an isolated antibody, or antigen binding fragment thereof, which specifically binds to an extracellular domain of CD300f, wherein the antibody, or antigen binding fragment thereof, comprises:
- (a) a heavy chain variable region which comprises:
  - (i) an amino acid sequence that is at least 70% identical to the amino acid sequence of the heavy chain variable region of monoclonal antibody DCR-2; or
  - (ii) a complementarity determining region 1 (CDR1) that is identical to CDR1 of the heavy chain variable region of monoclonal antibody DCR-2, a complementarity determining region 2 (CDR2) that is identical to CDR2 of the heavy chain variable region of monoclonal antibody DCR-2, and/or a complementarity determining region 3 (CDR3) that is identical to CDR3 of the heavy chain variable region of monoclonal antibody DCR-2; and/or
- (b) a light chain variable region which comprises:
  - (i) an amino acid sequence that is at least 70% identical to the amino acid sequence of the light chain variable region of monoclonal antibody DCR-2; or
  - (ii) a complementarity determining region 1 (CDR1) that is identical to CDR1 of the light chain variable region of monoclonal antibody DCR-2, a complementarity determining region 2 (CDR2) that is identical to CDR2 of the light chain variable region of monoclonal antibody DCR-2, and/or a complementarity determining region 3 (CDR3) that is identical to CDR3 of the light chain variable region of monoclonal antibody DCR-2.

An eighth aspect provides an immunoconjugate comprising an isolated antibody, or antigen binding fragment thereof, which specifically binds to an extracellular domain of CD300f, wherein the antibody, or antigen binding fragment thereof, comprises:
- (a) a heavy chain variable region which comprises:
  - (i) an amino acid sequence that is at least 70% identical to the amino acid sequence of the amino acid sequence represented by SEQ ID NO: 1; or
  - (ii) a complementarity determining region 1 (CDR1) that comprises the amino acid sequence represented by SEQ ID NO: 2, a complementarity determining region 2 (CDR2) that comprises an amino acid sequence that is represented by SEQ ID NO: 3, and/or a complementarity determining region 3 (CDR3) that comprises an amino acid sequence that is represented by SEQ ID NO: 4; and/or
- (b) a light chain variable region which comprises:
  - (i) an amino acid sequence that is at least 70% identical to the amino acid sequence represented by SEQ ID NO: 5; or
  - (ii) a complementarity determining region 1 (CDR1) that comprises an amino acid sequence represented by SEQ ID NO: 6, a complementarity determining region 2 (CDR2) that comprises an amino acid sequence represented by SEQ ID NO: 7, and/or a complementarity determining region 3 (CDR3) that comprises an amino acid sequence represented by SEQ ID NO: 8, wherein the antibody, or antigen binding fragment thereof, is coupled to a moiety.

A ninth aspect provides an immunoconjugate comprising an isolated antibody, or antigen binding fragment thereof, which specifically binds to an extracellular domain of CD300f, wherein the antibody, or antigen binding fragment thereof, comprises a heavy chain variable region which comprises the amino acid sequence represented by SEQ ID NO: 1, and/or a light chain variable region which comprises the amino acid sequence represented by SEQ ID NO: 5, wherein the antibody, or antigen binding fragment thereof, is coupled to a moiety.

A tenth aspect provides an immunoconjugate comprising an isolated antibody, or antigen binding fragment thereof, which specifically binds to an extracellular domain of CD300f, wherein the antibody, or antigen binding fragment thereof, comprises:
- (a) a heavy chain variable region which comprises:
  - (i) an amino acid sequence that is at least 70% identical to the amino acid sequence of the heavy chain variable region of monoclonal antibody DCR-2; or
  - (ii) a complementarity determining region 1 (CDR1) that is identical to CDR1 of the heavy chain variable region of monoclonal antibody DCR-2, a complementarity determining region 2 (CDR2) that is identical to CDR2 of the heavy chain variable region of monoclonal antibody DCR-2, and/or a complementarity determining region 3 (CDR3) that is identical to CDR3 of the heavy chain variable region of monoclonal antibody DCR-2; and/or
- (b) a light chain variable region which comprises:
  - (i) an amino acid sequence that is at least 70% identical to the amino acid sequence of the light chain variable region of monoclonal antibody DCR-2; or
  - (ii) a complementarity determining region 1 (CDR1) that is identical to CDR1 of the light chain variable region of monoclonal antibody DCR-2, a complementarity determining region 2 (CDR2) that is identical to CDR2 of the light chain variable region of monoclonal antibody DCR-2, and/or a complementarity determining region 3 (CDR3) that is identical to CDR3 of the light chain variable region of monoclonal antibody DCR-2, and wherein the antibody, or antigen binding fragment thereof, is coupled to a moiety.

An eleventh aspect provides a composition comprising the antibody, or antigen binding fragment thereof, of any one of the first to sixth aspects, or an immunoconjugate of the seventh to ninth aspects.

A twelfth aspect provides a nucleic acid encoding a polypeptide, which comprises:
(a) a heavy chain variable region which comprises:
 (i) an amino acid sequence that is at least 70% identical to the amino acid sequence of the amino acid sequence represented by SEQ ID NO: 1; and/or
 (ii) a complementarity determining region 1 (CDR1) that comprises the amino acid sequence represented by SEQ ID NO: 2, a complementarity determining region 2 (CDR2) that comprises an amino acid sequence that is represented by SEQ ID NO: 3, and/or a complementarity determining region 3 (CDR3) that comprises an amino acid sequence that is represented by SEQ ID NO: 4; and/or
(b) a light chain variable region which comprises:
 (i) an amino acid sequence that is at least 70% identical to the amino acid sequence represented by SEQ ID NO: 5; and/or
 (ii) a complementarity determining region 1 (CDR1) that comprises an amino acid sequence represented by SEQ ID NO: 6, a complementarity determining region 2 (CDR2) that comprises an amino acid sequence represented by SEQ ID NO: 7, and/or a complementarity determining region 3 (CDR3) that comprises an amino acid sequence represented by SEQ ID NO: 8.

A thirteenth aspect provides a nucleic acid sequence encoding a polypeptide which comprises the amino acid sequence represented by SEQ ID NO: 1, and/or the amino acid sequence represented by SEQ ID NO: 5.

A fourteenth aspect provides a nucleic acid encoding an antibody, or antigen binding fragment thereof, of the first to seventh aspects.

A fifteenth aspect provides a cell comprising a nucleic acid of the twelfth to fourteenth aspect.

A sixteenth aspect provides a method of treating a condition associated with CD300f expression in a subject in need thereof, comprising administering to the subject an effective amount of an antibody, or antigen binding fragment thereof, of the first to seventh aspects, an immunoconjugate of the eighth to tenth aspects, a composition of the eleventh aspect, or a cell of the fifteenth aspect.

An alternative sixteenth aspect provides an antibody, or antigen binding fragment thereof, of the first to seventh aspects, an immunoconjugate of the eighth to tenth aspects, a composition of the eleventh aspect, or a cell of the fifteenth aspect, for use in treating a condition associated with CD300f expression in a subject in need thereof, or use of an antibody, or antigen binding fragment thereof, of the first to seventh aspects, an immunoconjugate of the eighth to tenth aspects, a composition of the eleventh aspect, or a cell of the fifteenth aspect, in the manufacture of a medicament for treating a condition associated with CD300f expression in a subject in need thereof.

A seventeenth aspect provides a kit comprising an antibody, or antigen binding fragment thereof, of the first to seventh aspects, an immunoconjugate of the eighth to tenth aspects, a composition of the eleventh aspect, a nucleic acid of the twelfth to fourteenth aspect, or a cell of the fifteenth aspect.

An eighteenth aspect provides a hybridoma deposited under the Budapest Treaty on 27 Sep. 2016 at CellBank Australia and allocated accession no. CBA20160029.

A nineteenth aspect provides an antibody, or antigen binding fragment thereof, which cross-competes with DCR-2 for binding to an extracellular domain of CD300f.

A twentieth aspect provides an expression vector expressing the nucleic acid of the twelfth to fourteenth aspect.

A twenty first aspect provides a cell comprising an expression vector of the twentieth aspect.

A twenty second aspect provides a monoclonal antibody produced by the hybridoma deposited under the Budapest Treaty on 27 Sep. 2016 at CellBank Australia and allocated accession no. CBA20160029.

A twenty third aspect provides a method of producing an antibody, or antigen binding fragment thereof, which specifically binds to an extracellular domain of CD300f, comprising:
(a) incubating a cell of the fifteenth aspect, or a hybridoma of the eighteenth aspect, under conditions which permit production of antibody, or an antigen binding fragment thereof; and
(b) isolating the antibody, or an antigen binding fragment thereof, produced in step (a).

BRIEF DESCRIPTION OF THE DRAWINGS

FIG. 1B is a graph showing binding of DCR-2 and commercially available CD300f antibodies to CD300f-Ig fusion protein as determined by ELISA; FIG. 1C is a graph showing binding of DCR-2 and commercially available CD300f antibodies to CD300b-Ig fusion protein as determined by ELISA.

FIGS. 3A-3C are a comparison of DCR-2 and commercially available CD300f antibodies UP-D1, UP-D2, 234903, CML-1 and gLMIR3 binding to: (A) healthy PBMC populations assessed by multiparameter flow cytometry; (B) AML blasts and CD34$^+$CD38$^-$ leukaemic stem cells (LSCs) (n=5); and (C) Lin-CD34+CD38CD45RA− CD90+ cord blood hematopoietic stem cells (n=3). The geometric MFI of the population of interest was divided by the geometric MFI of the isotype control to give a "geometric MFI ratio". Lineage antibodies (Lin) includes monoclonal antibodies to CD3, CD19, CD20, CD56 and CD14.

FIG. 9 shows the results of Bio-Layer Interferometry analysis of DCR-2. DCR-2 was assessed for affinity for CD300f using a BLItz System (Fortebio, Pall Life Sciences). CD300f-Fc recombinant protein was immobilized in a human IgG Fc capture sensor. A five point dilution series of each mAb was tested for association and dissociation. Kinetic rate constants were estimated using BLItz Pro software with a global fitting 1:1 binding model. A shows the run conditions, and B shows the analysis of the data.

FIG. 12 shows an alignment of the amino acid sequence of the mouse heavy chain variable region of DCR-2 (A), and predicted humanised mouse heavy chain variable region of DCR-2 (B). CDR1, CDR2 and CD3 sequences are shown in dashed boxes as indicated. Amino acids of the mouse sequence that have been replaced with human sequence are underlined and in bold.

DETAILED DESCRIPTION

Figure 1:
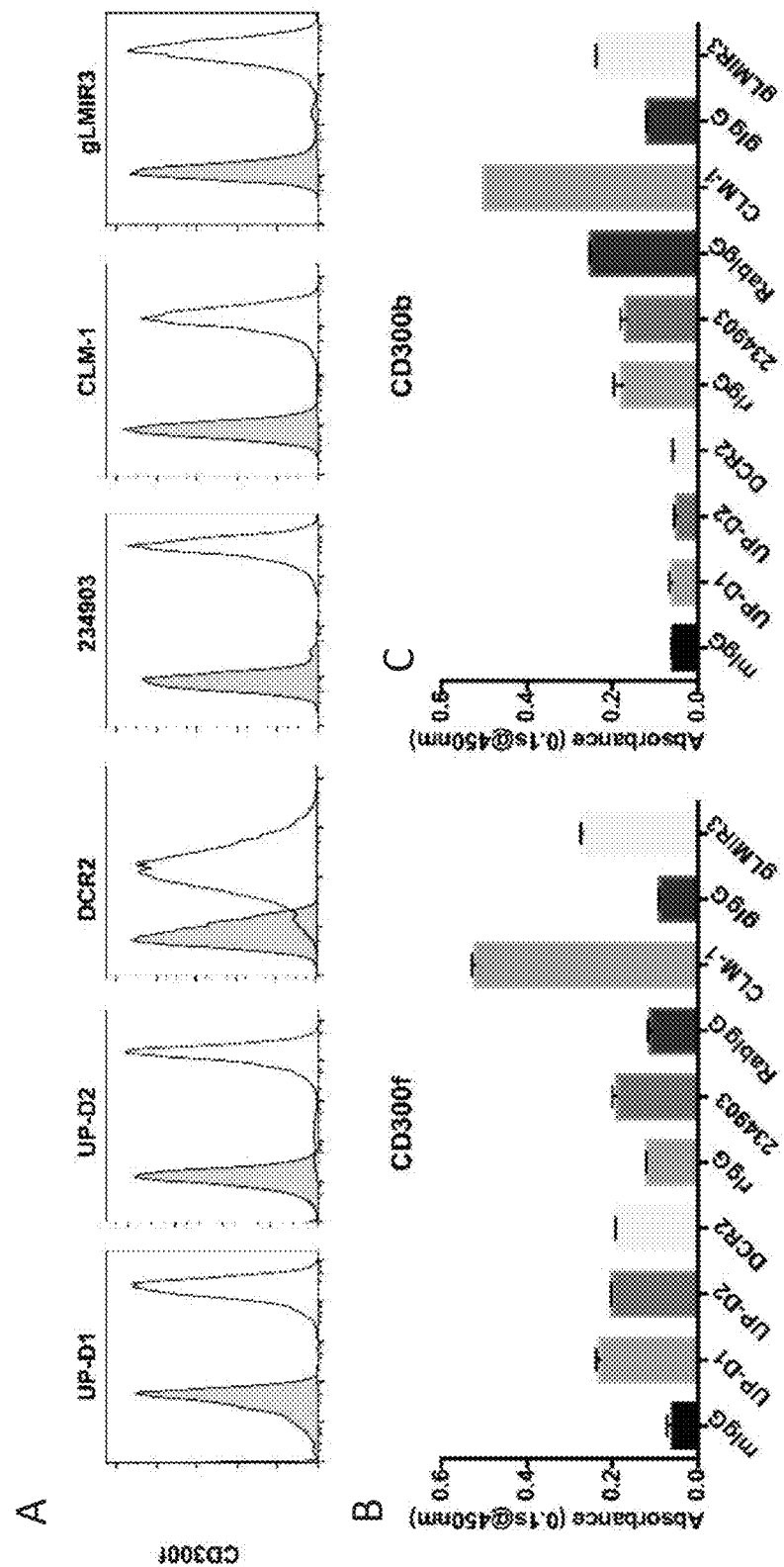
FIGS. 1A to 1C are graphs showing the specificity of DCR-2 and commercially available CD300f antibodies (UP-D1, UP-D2, 234903, CML-1 and gLMIR3). (A) FIG. 1A are histograms showing the result of binding of DCR-2 and commercially available CD300f antibodies to CD300f transfected CHO cells as determined by flow cytometry. Antibody binding (unshaded histogram) was compared to the relevant isotype for each antibody (shaded histogram).

CD300f is a member of the CD300 family of immunoregulatory molecules encoded by a gene complex on human chromosome 17q25. CD300f is a transmembrane glycoprotein with a cytoplasmic region that contains both inhibitory immunoreceptor tyrosine inhibitory motifs (ITIMs) and phosphatidylinositide-3-kinase (PI3K) phosphorylation sites. Like other members of the family, CD300f is a transmembrane glycoprotein with a single Ig-like extracellular domain.

As described herein, the inventors have isolated a monoclonal antibody which binds specifically to the extracellular domain of CD300f. The monoclonal antibody is referred to herein as DCR-2. A hybridoma producing DCR-2 was deposited at CellBank Australia, 214 Hawkesbury Rd., Westmead, NSW 2145, Australia, under the Budapest Treaty on 27 Sep. 2016 and designated accession number CBA20160029.

As described herein, DCR-2 binds multiple isoforms of CD300f that are expressed by AML and CD34$^+$CD38$^-$ leukemic stem cells (LSCs). In this regard, DCR-2 binds isoforms of CD300f which comprise the sequence STPAPTTPTSTTFT (CD300f$^{L4}$) and isoforms of CD300f in which the sequence STPAPTTPTSTTFT is absent (CD300f$^{S4}$).

As also described herein, DCR-2 enhances the binding of the commercially available CD300f monoclonal antibody UP-D2 to cells expressing CD300f. DCR-2 may therefore be used in conjunction with UP-D2 to enhance the binding and uptake of UP-D2 into a cell expressing CD300f. Enhancing the binding of UP-D2 or UP-D2 immunoconjugates to cells expressing CD300f using DCR-2 may enhance the delivery of therapeutic and/or diagnostic moieties into cells expressing CD300f, such as AML cells and leukemic stem cells.

As further described herein, DCR-2 itself exhibits antibody dependent cell-mediated cytotoxicity (ADCC) in the human promyelocytic leukemia cell line HL-60.

The present disclosure therefore relates in one aspect to an isolated antibody, or antigen binding fragment thereof, that specifically binds to an extracellular domain of CD300f (also referred to herein as the DCR-2 antibody or antigen binding fragment thereof), wherein the antibody or antigen binding fragment thereof comprises:
(a) a heavy chain variable region which comprises:
(i) an amino acid sequence that is at least 70% identical, typically at least 75%, 80%, 85%, 90%, 95%, 96%, 97%, 98% or 99% identical, to the amino acid sequence of the heavy chain variable region of monoclonal antibody DCR-2; or
(ii) a complementarity determining region 1 (CDR1) that is identical to CDR1 of the heavy chain variable region of monoclonal antibody DCR-2, a complementarity determining region 2 (CDR2) that is identical to CDR2 of the heavy chain variable region of monoclonal antibody DCR-2, and/or a complementarity determining region 3 (CDR3) that is identical to CDR3 of the heavy chain variable region of monoclonal antibody DCR-2; and/or (b) a light chain variable region which comprises:
(i) an amino acid sequence that is at least 70% identical, typically at least 75%, 80%, 85%, 90%, 95%, 96%, 97%, 98% or 99% identical, to the amino acid sequence of the light chain variable region of monoclonal antibody DCR-2; or
(ii) a complementarity determining region 1 (CDR1) that is identical to CDR1 of the light chain variable region of monoclonal antibody DCR-2, a complementarity determining region 2 (CDR2) that is identical to CDR2 of the light chain variable region of monoclonal antibody DCR-2, and/or a complementarity determining region 3 (CDR3) that is identical to CDR3 of the light chain variable region of monoclonal antibody DCR-2.

The inventors have determined the nucleotide and amino acid sequence of the heavy chain variable region of DCR-2 and the light chain variable region of DCR-2.

TABLE 1

Antibody sequences referred to in the sequence listing

| SEQ ID NO: | Description |
| --- | --- |
| 1 | amino acid sequence of heavy chain variable region of DCR-2 |
| 2 | amino acid sequence of CDR1 of heavy chain variable region of DCR-2 |
| 3 | amino acid sequence of CDR2 of heavy chain variable region of DCR-2 |
| 4 | amino acid sequence of CDR3 of heavy chain variable region of DCR-2 |
| 5 | amino acid sequence of light chain variable region of DCR-2 |
| 6 | amino acid sequence of CDR1 of light chain variable region of DCR-2 |
| 7 | amino acid sequence of CDR2 of light chain variable region of DCR-2 |
| 8 | amino acid sequence of CDR3 of light chain variable region of DCR-2 |
| 9 | nucleotide sequence of heavy chain variable region of DCR-2 |
| 10 | nucleotide sequence of light chain variable region of DCR-2 |
| 11 | codon optimized nucleotide sequence encoding chimeric antibody heavy chain comprising the heavy chain variable region of DCR-2 combined with the constant region of the heavy chain of human anti-TNP IgG1. |
| 12 | codon optimized nucleotide sequence encoding chimeric antibody light chain comprising the light chain variable region of DCR-2 combined with the constant region of the kappa chain of human anti-TNP IgG1. |
| 13 | amino acid sequence encoded by SEQ ID NO: 11. |
| 14 | amino acid sequence encoded by SEQ ID NO: 12. |
| 15 | amino acid sequence of humanized heavy chain variable region of DCR-2 |

The amino acid sequence of the heavy chain variable region ($V_H$) of DCR-2 is represented by the amino acid sequence:

```
                                    (SEQ ID NO: 1)
MESGGGLVQPGGPLKLSCAASGFGFSGSWMS

WVRQAPGKGLEWIGQINPDSSTINYTPSLKDK

FIISRDNAKNTLYLQINKVRSEDTALYYCARRG

FFEGYSAWFAYW.
```

The amino acid sequence of CDR1 of the heavy chain variable region of DCR-2 is represented by the amino acid sequence GFGFSGSW (SEQ ID NO: 2).

The amino acid sequence of CDR2 of the heavy chain variable region of DCR-2 is represented by the amino acid sequence INPDSSTI (SEQ ID NO: 3).

The amino acid sequence of CDR3 of the heavy chain variable region of DCR-2 is represented by the amino acid sequence ARRGFFEGYSAWFAY (SEQ ID NO: 4).

The amino acid of the light chain variable region ($V_L$) of DCR-2 is represented by the amino acid sequence:

```
                                    (SEQ ID NO: 5)
ILMTQTPKFLLVSAGDRVTITCKASQSVSNDV

AWYQQKPGQSPSLLIYYASNRNTGVPDRFTG

SGYETDFTFTISTVQAEDLAVYFCQQDYTSPW

TFGGG.
```

The amino acid sequence of CDR1 of the light chain variable region of DCR-2 is represented by the amino acid sequence QSVSND (SEQ ID NO: 6).

The amino acid sequence of CDR2 of the light chain variable region of DCR-2 is represented by the amino acid sequence YAS (SEQ ID NO: 7).

The amino acid sequence of CDR3 of the light chain variable region of DCR-2 is represented by the amino acid sequence QQDYTSPWT (SEQ ID NO: 8).

The present disclosure therefore relates in one aspect to an isolated antibody, or antigen binding fragment thereof, that specifically binds to an extracellular domain of CD300f, wherein the antibody, or antigen binding fragment thereof, comprises:
(a) a heavy chain variable region which comprises:
(i) an amino acid sequence that is at least 70%, typically at least 75%, 80%, 85%, 90%, 95%, 96%, 97%, 98%, or 99% identical to the amino acid sequence represented by SEQ ID NO: 1; or
(ii) a complementarity determining region 1 (CDR1) that comprises the amino acid sequence GFGFSGSW (SEQ ID NO: 2), a complementarity determining region 2 (CDR2) that comprises the amino acid sequence INPDSSTI (SEQ ID NO: 3), and/or a complementarity determining region 3 (CDR3) that comprises the amino acid sequence ARRGFFEGYSAWFAY (SEQ ID NO: 4); and/or
(b) a light chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 5; or
(ii) a complementarity determining region 1 (CDR1) that comprises the amino acid sequence QSVSND (SEQ ID NO: 6), a complementarity determining region 2 (CDR2) that comprises the amino acid sequence YAS (SEQ ID NO: 7), and/or a complementarity determining region 3 (CDR3) that comprises the amino acid sequence QQDYTSPWT (SEQ ID NO: 8).

In one embodiment, the antibody or antigen binding fragment thereof comprises:
(a) a heavy chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 1; or
(ii) a complementarity determining region 1 (CDR1) that comprises the amino acid sequence represented by SEQ ID NO: 2, a complementarity determining region 2 (CDR2) that comprises the amino acid sequence represented by SEQ ID NO: 3, and/or a complementarity determining region 3 (CDR3) that comprises the amino acid sequence represented by SEQ ID NO: 4; and
(b) a light chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 5; or
(ii) a complementarity determining region 1 (CDR1) that comprises the amino acid sequence represented by SEQ ID NO: 6, a complementarity determining region 2 (CDR2) that comprises the amino acid sequence represented by SEQ ID NO: 7, and/or a complementarity determining region 3 (CDR3) that comprises the amino acid sequence represented by SEQ ID NO: 8.

In one embodiment, the antibody or antigen binding fragment thereof comprises:
(a) a heavy chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 1; and/or
(b) a light chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 5.

In one embodiment, the antibody, or antigen binding fragment thereof, comprises:
(a) a heavy chain variable region which comprises:
(i) a complementarity determining region 1 (CDR1) that comprises the amino acid sequence represented by SEQ ID NO: 2, a complementarity determining region 2 (CDR2) that comprises the amino acid sequence represented by SEQ ID NO: 3, and a complementarity determining region 3 (CDR3) that comprises the amino acid sequence represented by SEQ ID NO: 4; or
(b) a light chain variable region which comprises:
(i) a complementarity determining region 1 (CDR1) that comprises the amino acid sequence represented by SEQ ID NO: 6, a complementarity determining region 2 (CDR2) that comprises the amino acid sequence represented by SEQ ID NO: 7, and a complementarity determining region 3 (CDR3) that comprises the amino acid sequence represented by SEQ ID NO: 8.

In one embodiment, the antibody, or antigen binding fragment thereof, comprises:
(a) a heavy chain variable region which comprises:
(i) a complementarity determining region 1 (CDR1) that comprises the amino acid sequence represented by SEQ ID NO: 2, a complementarity determining region 2 (CDR2) that comprises the amino acid sequence represented by SEQ ID NO: 3, and a complementarity determining region 3 (CDR3) that comprises the amino acid sequence represented by SEQ ID NO: 4; and
(b) a light chain variable region which comprises:
(i) a complementarity determining region 1 (CDR1) that comprises the amino acid sequence represented by SEQ ID NO: 6, a complementarity determining, region 2 (CDR2) that is identical to the amino acid sequence represented by SEQ ID NO: 7, and a complementarity determining region 3 (CDR3) that comprises the amino acid sequence represented by SEQ ID NO: 8.

In one embodiment, the antibody, or antigen binding fragment thereof, comprises a heavy chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 1. In one embodiment, the heavy chain variable region comprises an amino acid sequence that is 100% identical to the amino acid sequence represented by SEQ ID NO: 1.

In one embodiment, the antibody, or antigen binding fragment thereof, comprises a light chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 5. In one embodiment, the light chain variable region comprises an amino acid sequence that is 100% identical to the amino acid sequence represented by SEQ ID NO: 5.

In various embodiments, the antibody, or antigen binding fragment thereof, which specifically binds CD300f comprises:
(a) a heavy chain variable region comprising the amino acid sequence represented by SEQ ID NO: 1;
(b) a heavy chain variable region comprising an amino acid sequence that is at least 70% identical, typically at least 75%, 80%, 85%, 90%, 95%, 96%, 97%, 98%, or 99% identical, to the amino acid sequence represented by SEQ ID NO: 1;
(c) a light chain variable region comprising the amino acid sequence represented by SEQ ID NO: 5;
(d) a light chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 5;
(e) a heavy chain variable region comprising the amino acid sequence represented by SEQ ID NO: 1, and a light chain variable region comprising the amino acid sequence represented by SEQ ID NO: 5;
(f) a heavy chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 1, and a light chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 5;
(g) a heavy chain CDR1 comprising the amino acid sequence represented by SEQ ID NO: 2;
(h) a heavy chain CDR2 comprising the amino acid sequence represented by SEQ ID NO: 3;
(i) a heavy chain CDR3 comprising the amino acid sequence represented by SEQ ID NO: 4;
(j) a heavy chain CDR1 comprising the amino acid sequence represented by SEQ ID NO: 2 and a heavy chain CDR2 comprising the amino acid sequence represented by SEQ ID NO: 3;
(k) a heavy chain CDR1 comprising the amino acid sequence represented by SEQ ID NO: 2 and a heavy chain CDR3 comprising the amino acid sequence represented by SEQ ID NO: 4;

(l) a heavy chain CDR2 comprising the amino acid sequence represented by SEQ ID NO: 3 and a heavy chain CDR3 comprising the amino acid sequence represented by SEQ ID NO: 4;
(m) a heavy chain CDR1 comprising the amino acid sequence represented by SEQ ID NO: 2, a heavy chain CDR2 comprising the amino acid sequence represented by SEQ ID NO: 3, and a heavy chain CDR3 comprising the amino acid sequence represented by SEQ ID NO: 4;
(n) a light chain CDR1 comprising the amino acid sequence represented by SEQ ID NO: 6;
(o) a light chain CDR2 comprising the amino acid sequence represented by SEQ ID NO: 7;
(p) a light chain CDR3 comprising the amino acid sequence represented by SEQ ID NO: 8;
(q) a light chain CDR1 comprising the amino acid sequence represented by SEQ ID NO: 6, and a light chain CDR2 comprising the amino acid sequence represented by SEQ ID NO: 7;
(r) a light chain CDR1 comprising the amino acid sequence represented by SEQ ID NO: 6, and a light chain CDR3 comprising the amino acid sequence represented by SEQ ID NO: 8;
(s) a light chain CDR2 comprising the amino acid sequence represented by SEQ ID NO: 7, and a light chain CDR3 comprising the amino acid sequence represented by SEQ ID NO: 8;
(t) a light chain CDR1 comprising the amino acid sequence represented by SEQ ID NO: 6, a light chain CDR2 comprising the amino acid sequence represented by SEQ ID NO: 7, and a light chain CDR3 comprising the amino acid sequence represented by SEQ ID NO: 8;
(u) a heavy chain CDR1 comprising the amino acid sequence represented by SEQ ID NO: 2, and a light chain CDR1 comprising the amino acid sequence represented by SEQ ID NO: 6;
(v) a heavy chain CDR2 comprising the amino acid sequence represented by SEQ ID NO: 3, and a light chain CDR2 comprising the amino acid sequence represented by SEQ ID NO: 7;
(w) a heavy chain CDR3 comprising the amino acid sequence represented by SEQ ID NO: 4, and a light chain CDR3 comprising the amino acid sequence represented by SEQ ID NO: 8;
(x) a heavy chain CDR1 comprising the amino acid sequence represented by SEQ ID NO: 2, a heavy chain CDR2 comprising the amino acid sequence represented by SEQ ID NO: 3, a light chain CDR1 comprising the amino acid sequence represented by SEQ ID NO: 6, and a light chain CDR2 comprising the amino acid sequence represented by SEQ ID NO: 7;
(y) a heavy chain CDR1 comprising the amino acid sequence represented by SEQ ID NO: 2, a heavy chain CDR3 comprising the amino acid sequence represented by SEQ ID NO: 4, a light chain CDR1 comprising the amino acid sequence represented by SEQ ID NO: 6, and a light chain CDR3 comprising the amino acid sequence represented by SEQ ID NO: 8;
(z) a heavy chain CDR2 comprising the amino acid sequence represented by SEQ ID NO: 3, a heavy chain CDR3 comprising the amino acid sequence represented by SEQ ID NO: 4, a light chain CDR2 comprising the amino acid sequence represented by SEQ ID NO: 7, and a light chain CDR3 comprising the amino acid sequence represented by SEQ ID NO: 8;
(aa) a heavy chain CDR1 comprising the amino acid sequence represented by SEQ ID NO: 2, a heavy chain CDR2 comprising the amino acid sequence represented by SEQ ID NO: 3, a heavy chain CDR3 comprising the amino acid sequence represented by SEQ ID NO: 4, a light chain CDR1 comprising the amino acid sequence represented by SEQ ID NO: 6, a light chain CDR2 comprising the amino acid sequence represented by SEQ ID NO: 7, and a light chain CDR3 comprising the amino acid sequence represented by SEQ ID NO: 8;
(bb) a heavy chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 1, and comprises a CDR1 comprising the amino acid sequence represented by SEQ ID NO: 2, a CDR2 comprising the amino acid sequence represented by SEQ ID NO: 3, and a CDR3 comprising the amino acid sequence represented by SEQ ID NO: 4;
(cc) a light chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 5, and comprises a CDR1 comprising the amino acid sequence represented by SEQ ID NO: 6, a CDR2 comprising the amino acid sequence represented by SEQ ID NO: 7, and a CDR3 comprising the amino acid sequence represented by SEQ ID NO: 8;
(dd) a heavy chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 1, and comprises a CDR1 comprising the amino acid sequence represented by SEQ ID NO: 2, a CDR2 comprising the amino acid sequence represented by SEQ ID NO: 3, and a CDR3 comprising the amino acid sequence represented by SEQ ID NO: 4, and a light chain variable region which comprises an amino acid sequence that is at least 70% identical, typically at least 75%, 80%, 85%, 90%, 95%, 96%, 97%, 98%, or 99% identical, to the amino acid sequence represented by SEQ ID NO: 5, and comprises a CDR1 comprising the amino acid sequence represented by SEQ ID NO: 6, a CDR2 comprising the amino acid sequence represented by SEQ ID NO: 7, and a CDR3 comprising the amino acid sequence represented by SEQ ID NO: 8.

In one embodiment, the antibody, or antigen binding fragment thereof, comprises a heavy chain comprising the amino acid sequence represented by SEQ ID NO: 13.

In one embodiment, the antibody, or antigen binding fragment thereof, comprises a light chain variable region comprising the amino acid sequence represented by SEQ ID NO: 14.

In one embodiment, the antibody, or antigen binding fragment thereof, that specifically binds to CD300f, comprises a heavy chain variable region which comprises an amino acid sequence that is at least 90% identical to the amino acid sequence represented by SEQ ID NO: 1, and a light chain variable region which comprises an amino acid sequence that is at least 90% identical to the amino acid sequence represented by SEQ ID NO: 5.

In one embodiment, the antibody, or antigen binding fragment thereof, that specifically binds to CD300f, comprises a heavy chain variable region which comprises an amino acid sequence that is at least 95% identical to the amino acid sequence represented by SEQ ID NO: 1, and a light chain variable region which comprises an amino acid sequence that is at least 95% identical to the amino acid sequence represented by SEQ ID NO: 5.

In one embodiment, the antibody, or antigen binding fragment thereof, that specifically binds to CD300f, comprises: a heavy chain variable region which comprises a CDR1 comprising the amino acid sequence represented by SEQ ID NO: 2, a CDR2 comprising the amino acid sequence represented by SEQ ID NO: 3, and a CDR3 comprising the amino acid sequence represented by SEQ ID NO: 4; and a light chain variable region which comprises a CDR1 comprising the amino acid sequence represented by SEQ ID NO: 6, a CDR2 comprising the amino acid sequence represented by SEQ ID NO: 7, and a CDR3 comprising the amino acid sequence represented by SEQ ID NO: 8.

In one embodiment, the antibody, or antigen binding fragment thereof, that specifically binds to CD300f, comprises: a heavy chain variable region which comprises an amino acid sequence that is at least 90% identical to the amino acid sequence represented by SEQ ID NO: 1, and comprises a CDR1 comprising the amino acid sequence represented by SEQ ID NO: 2, a CDR2 comprising the amino acid sequence represented by SEQ ID NO: 3, and a CDR3 comprising the amino acid sequence represented by SEQ ID NO: 4; and a light chain variable region which comprises an amino acid sequence that is at least 90% identical to the amino acid sequence represented by SEQ ID NO: 1, and comprises a CDR1 comprising the amino acid sequence represented by SEQ ID NO: 6, a CDR2 comprising the amino acid sequence represented by SEQ ID NO: 7, and a CDR3 comprising the amino acid sequence represented by SEQ ID NO: 8.

In one embodiment, the antibody, or antigen binding fragment thereof, that specifically binds to CD300f, comprises: a heavy chain variable region which comprises an amino acid sequence that is at least 95% identical to the amino acid sequence represented by SEQ ID NO: 1, and comprises a CDR1 comprising the amino acid sequence represented by SEQ ID NO: 2, a CDR2 comprising the amino acid sequence represented by SEQ ID NO: 3, and a CDR3 comprising the amino acid sequence represented by SEQ ID NO: 4; and a light chain variable region which comprises an amino acid sequence that is at least 95% identical to the amino acid sequence represented by SEQ ID NO: 1, and comprises a CDR1 comprising the amino acid sequence represented by SEQ ID NO: 6, a CDR2 comprising the amino acid sequence represented by SEQ ID NO: 7, and a CDR3 comprising the amino acid sequence represented by SEQ ID NO: 8.

The percent identity between two amino acid sequences can be determined using any alignment algorithms known in the art, including for example, the FASTA package of sequence analysis programs (Lipman & Pearson, (1985) Science 227(4693): 1435-1441); BLAST (Altschul et al. J. Mol. Biol. 215(3):403-410.

In one embodiment, the antibody, or antigen binding fragment thereof, binds to human CD300f with an equilibrium dissociation constant (KO of less than $10^{-7}$M, typically less than $10^{-8}$M, less than $10^{-9}$M, less than $9 \times 10^{-10}$M, less than $8 \times 10^{-10}$, less than $7 \times 10^{-10}$, less than $6 \times 10^{-10}$, less than $5 \times 10^{-10}$, or less than $4 \times 10^{-10}$ M.

In one embodiment, the antibody, or antigen binding fragment thereof, binds to human CD300f with an equilibrium dissociation constant ($K_D$) that is in the range of from $1 \times 10^{-10}$ to $1 \times 10^{-7}$M, typically in the range of from $1 \times 10^{-10}$ to $1 \times 10^{-7}$ M, $1 \times 10^{-10}$ to $1 \times 10^{-8}$ M, $1 \times 10^{-10}$ to $1 \times 10^{-9}$ M, $1 \times 10^{-10}$ to $9 \times 10^{-10}$ M, $1 \times 10^{-10}$ to $8 \times 10^{-10}$ M or $1 \times 10^{-10}$ to $7 \times 10^{-10}$ M, $2 \times 10^{-10}$ to $6 \times 10^{-10}$ M, or $3 \times 10^{-10}$ to $5 \times 10^{-10}$ M.

In one embodiment, the antibody, or antigen binding fragment thereof, binds to human CD300f with a $K_A$ of about $1 \times 10^6$ $M^{-1}s^{-1}$ or less. In various embodiments, the antibody or antigen binding fragment thereof binds to human CD300f with a $K_A$ in the range of from $1 \times 10^5$ to $5 \times 10^6$ $M^{-1}s^{-1}$, typically $1 \times 10^5$ to $1 \times 10^6$ $M^{-1}s^{-1}$.

In one embodiment, the antibody, or antigen binding fragment thereof, binds to human CD300f with an off rate of $5 \times 10^{-2}$ $s^{-1}$ or less, typically $1 \times 10^{-2}$ $s^{-1}$ or less, $5 \times 10^{-3}$ $s^{-1}$ or less, $1 \times 10^{-3}$ $s^{-1}$ or less, or $5 \times 10^{-4}$ $s^{-1}$ or less, $4 \times 10^4$ $s^{-1}$ or less, $3 \times 10^{-4}$ $s^{-1}$ or less, or $2 \times 10^{-4}$ $s^1$ or less.

In one embodiment, the antibody, or antigen binding fragment thereof, binds to human CD300f with an off rate in the range of from $5 \times 10^{-2}$ $s^{-1}$ to $1 \times 10^{-5}$ $s^{-1}$, $1 \times 10^{-2}$ to $5 \times 10^{-5}$ $s^{-1}$, $5 \times 10^{-3}$ to $5 \times 10^{-4}$ $s^{-1}$, $1 \times 10^3$ to $5 \times 10^4$ $s^{-1}$, or $1 \times 10^{-3}$ to $1 \times 10^{-4}$ $s^{-1}$.

Another aspect provides a hybridoma deposited under the Budapest Treaty on 27 Sep. 2016 at CellBank Australia, 214 Hawkesbury Road, Westmead, NSW 2145, Australia, and designated accession no. CBA20160029. The hybridoma deposited under the Budapest Treaty and designated accession no. CNA20160029 expresses DCR-2.

Another aspect provides an antibody produced by the hybridoma deposited under the Budapest Treaty and designated accession number CNA20160029.

An antibody refers to an immunoglobulin molecule capable of specifically binding to an antigen. The antibody may be recombinant or modified, including chimeric, humanised, deimmunised, CDR-grafted, synhumanised, bi-specific, human. A full length antibody typically comprises two light chains covalently linked to two heavy chains. Each heavy chain of the full length antibody comprises a heavy chain variable region and a heavy chain constant region. Each light chain of a full length antibody comprises a light chain variable region and a light chain constant region. Full length antibodies may be any of the following type: IgG, IgM, IgE, IgD, IgA. In one embodiment, the antibody is IgG.

As used herein, an "antigen binding fragment" of an antibody comprises an antigen binding domain of the antibody, and typically comprises a portion of the antibody that specifically binds the same epitope as the full-length antibody. Typically, the antibody fragment of an antibody comprises portions of the variable region of the heavy and/or the light chain of the antibody. Typically, the antigen binding fragment comprises the CDR1, 2 and/or 3 region of the heavy chain variable region and/or the CDR1, 2 and/or 3 region of the light chain variable region. More typically, the antigen binding fragment comprises the CDR1, 2 and 3 region of the heavy chain variable region and/or the CDR1, 2 and 3 region of the light chain variable region. Still more typically, the antigen binding fragment comprises the CDR1, 2 and 3 region of the heavy chain variable region, and the CDR1, 2 and 3 region of the light chain variable region. In some embodiments, the antigen binding fragment of an antibody comprises the heavy chain variable region and the light chain variable region of an antibody. The portions of the heavy and light chain variable regions may be on separate polypeptide chains, such as Fv fragments, or in a single polypeptide chain in which the light chain and heavy chain variable regions are connected by a peptide linker ("scFv proteins"). Examples of antigen binding fragments of an antibody may include F(ab')2, Fab', Fab, Fv, sFv, scFv, and the like.

As used herein, an antigen binding fragment of an antibody encompasses one or more polypeptides which comprise an antigen binding domain of the antibody, such as an F(ab')2, Fab', Fab, Fv, sFv, or scFv.

An "antigen binding domain" refers to a region of an antibody that is capable of specifically binding to an antigen. Typically, the antigen binding domain comprises CDR1, CDR2 and/or CDR3 from the light chain variable region, and/or CDR1, CDR2 and/or CDR3 from the heavy chain variable region, of an antibody. More typically, the antigen binding domain comprises CDR1, CDR2 and CDR3 from the light chain variable region, and/or CDR1, CDR2 and/or CDR3 from the heavy chain variable region, of an antibody. Still more typically, the antigen binding domain comprises CDR1, CDR2 and CDR3 from the light chain variable region, and CDR1, CDR2 and CDR3 from the heavy chain variable region, of an antibody.

The term "variable region" refers to the portion of the light and/or heavy chain of an antibody that is capable of specifically binding to an antigen. The variable region comprises the complementarity determining regions (CDRs) and the framework regions (FRs). Framework regions are those variable regions other than the complementarity determining regions.

The term "complementarity determining region" refers to one of three amino acid sequences of the variable region of the light chain variable region and/or heavy chain variable region of an antibody that is largely responsible for the ability of the antibody to bind specifically to an antigen. The three complementarity determining regions of the variable region of the light and heavy chain are referred to as CDR1, CDR2 and CDR3.

Methods for determining the CDR regions and the framework (FR) regions of the variable region of the light and heavy chain are known in the art. For example, the amino acid positions assigned to CDRs and FRs may be defined according to Kabat Sequences of Proteins of Immunological Interest, National Institute of Health, Bethesda, MD, 1987 and 1991; Enhanced Clothia Numbering Scheme; Clothia and Lesk J. Mol. Biol. 196:901-917; Clothia et al. Nature 342: 877-883; Honnegher and Plukthun, J. Mol. Biol. 309: 657-670. The antibody, or antigen binding fragment thereof, specifically binds to the extracellular domain of CD300f. As used herein, "an antibody, or antigen binding fragment thereof, that specifically binds to an extracellular domain of CD300f" is an antibody or antigen binding fragment thereof that associates with the extracellular domain of CD300f more frequently, more rapidly, for greater length of time, or with greater affinity, that with other antigens.

The variable domains from antibodies may be cloned using conventional techniques that are known in the art and described in, for example, Sambrook and Russell, Eds, Molecular Cloning: A Laboratory Manual, 3rd Ed, vols. 1-3, Cold Spring Harbor Laboratory Press, 2001. In general, the light chain variable region and heavy chain variable region sequences for antibodies, such as murine antibodies, can be obtained by a variety of molecular cloning procedures, such as RT-PCR, 5'-RACE, and cDNA library screening.

As used herein, a chimeric antibody is an antibody protein that comprises the complementarity determining regions (CDRs), typically the variable regions, of an antibody derived from one species, typically a mouse antibody, while the constant domains of the antibody molecule, and in some embodiments, the framework regions (FR), are derived from another species, such as a human.

A humanised antibody is a form of chimeric antibody in which the amino acid sequence of the CDRs is from an antibody from one species; e.g., a mouse antibody, and the amino acid sequence of the constant regions, and typically the framework regions, is from a human antibody.

In one embodiment, the antibody or antigen binding fragment thereof is a chimeric antibody. The chimeric antibody comprises the complementarity-determining regions (CDRs), and typically framework regions (FR), of DCR-2. The chimeric antibody may comprise the light and heavy chain constant regions of a human antibody. The use of antibody components derived from chimerized monoclonal antibodies reduces potential problems associated with the immunogenicity of murine constant regions. Typically, the antibody is a humanised antibody. Humanization of murine antibodies and antibody fragments is known to those skilled in the art, and described in, for example, U.S. Pat. Nos. 5,225,539; 6,054,297; and 7,566,771. For example, humanized monoclonal antibodies may be produced by transferring murine complementary determining regions from heavy and light variable chains of the mouse immunoglobulin into a human variable domain, and then, substituting human residues in the framework regions of the murine counterparts. The use of human framework region sequences, in addition to human constant region sequences, further reduces the chance of inducing HAMA reactions.

Antibodies can be isolated and purified from serum and hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in Methods in Molecular Biology, Vol. 10, pages 79-104 (The Humana Press, Inc. 1992).

In some embodiments, an antigen binding fragment of an antibody includes portions of the variable region of the heavy and/or light chain of the antibody. The portions of the heavy chain variable region and/or light chain variable region may be on separate polypeptide chains, such as Fv fragments, or in a single polypeptide chain in which light and heavy variable regions are connected by a peptide linker (e.g. scFv proteins). Examples of antibody fragments include F(ab')$_2$, Fab', Fab, Fv, sFv, scFv, and the like. Typically, the antibody fragment comprises the CDR1, 2 and 3 region of the heavy chain variable region and/or the CDR1, 2 and 3 region of the light chain variable region. Antibody fragments which recognize specific epitopes can be generated by known techniques. F(ab')2 fragments, for example, can be produced by pepsin digestion of the antibody molecule. These and other methods are described, for example, by Coligan at pages 2.8.1-2.8.10 and 2.10.-2.10.4. Alternatively, Fab' expression libraries can be constructed to allow rapid and easy identification of Fab' fragments with the desired specificity.

In some embodiments, an antigen binding fragment of an antibody may be a single chain Fv molecule (scFv). A single chain Fv molecule (scFv) typically comprises a light chain variable region and a heavy chain variable region. The light chain variable region and heavy chain variable region are typically covalently linked by a peptide linker (L) and fold to form an antigen binding site. While the heavy chain variable region and light chain variable region may be directly joined together, those skilled in the art will appreciate that the regions may be separated by a peptide linker consisting of one or more amino acids. Peptide linkers and their use are known in the art. Generally the peptide linker will have no specific biological activity other than to join the regions or to preserve some minimum distance or other spatial relationship between the heavy chain variable region and light chain variable region. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length.

Methods of making scFv antibodies are known in the art, and have been described in, for example, U.S. Pat. No. 5,260,203. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Methods for preparing other antigen binding fragments of antibodies are known in the art. For example, antigen binding fragments can also be prepared by proteolytic hydrolysis of a full-length antibody or by expression in *E. coli* or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 Kd fragment denoted F(ab')$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the epitope that is recognized by the intact antibody.

In one embodiment, the antibody, or antigen binding fragment thereof, is a bispecific antibody. Bispecific antibodies are monoclonal, preferably human or humanized, antibodies that have binding specificities for at least two different antigens or that have binding specificities for two epitopes on the same antigen. In various embodiments, the bispecific antibody comprises (a) a binding specificity of DCR-2 and the binding specificity of UP-D2; (b) the binding specificity of DCR-2 and the binding specificity of CD3; (c) the binding specificity of DCR-2 and the binding specificity of another cancer antigen, typically an AML antigen, such as CD123, CD96, CD44, CD47 or CD33.

In some embodiments, the bispecific antibodies are bi-specific T-cell engagers. Bi-specific T-cell engagers (BiTEs) are a class of artificial bispecific monoclonal antibodies. BiTEs are fusion proteins, typically comprising two single-chain variable fragments (scFvs) of different antibodies, or amino acid sequences from four different genes, on a single peptide chain. One of the scFvs binds to a tumor antigen (e.g. CD300f) and the other generally to an effector cell, such as a T cell via the CD3 receptor. Method for preparing bispecific antibodies are described in, for example, Laszlo et al. Blood. 2014 Jan. 23; 123(4): 554-561; Loffler, Blood (2000), 95: 2098-103.

In another embodiment, the antibody, or antigen binding fragment thereof, is a chimeric antigen receptor for chimeric antigen receptor T cells (CAR T cells). In this regard, nucleic acid encoding a polypeptide comprising an antigen binding domain, such as a scFv, in conjunction with a signaling molecule, can be used to transduce T cells to produce CAR T cells. The antigen binding domain expressed in the CAR T cells is able to recognize an antigen in a non-MHC restricted manner. Accordingly, expression of, for example, scFv encoding the antigen binding domain of antibodies described herein, on the surface of T cells, may be effective in targeting, for example, AML cells or leukaemic stem cells. Methods for the preparation of CAR T cells are known in the art and described in, for example, Shannon et al. Blood, 25 Jun. 2015 Volume 125, No. 26: 4017-4023; O'Hear et al. (2015) Haematologica; 100(3): 336-344. Thus, in one aspect, there is provided a cell which comprises a nucleic acid encoding a polypeptide comprising the DCR-2 antibody, or antigen binding fragment thereof, described herein. Typically, the cell comprises a nucleic acid which encodes a polypeptide comprising an antigen binding domain of the DCR-2 antibody, such as an scFv comprising the amino acid sequence represented by SEQ ID NO: 1 and SEQ ID NO: 5. In one embodiment, the cell is a T-cell. In one embodiment, the polypeptide comprising the DCR-2 antibody or antigen binding fragment thereof described herein comprises an antigen binding domain of the DCR-2 antibody or antigen binding fragment thereof described herein and an endodomain. Examples of endodomains include T cell receptor zeta chain, CD3-zeta, CD3-zeta-CD28, CD3-zeta-CD28-OX40. Typically, the endodomain comprises a transmembrane domain. The transmembrane domain typically comprises a hydrophobic alpha helix which spans the cell membrane.

The DCR-2 antibodies, or antigen binding fragments thereof, described herein may be used to isolate other antibodies, or antigen binding fragments thereof, which bind the same epitope, or overlapping epitopes, by assessing cross-competition for the epitope. Cross-competition with the antibody or antigen binding fragments described herein can be assessed using methods known in the art, such as BIAcore analysis, flow cytometry, ELISA analysis. Accordingly, in another aspect, there is provided an antibody, or antigen binding fragment thereof, which cross-competes with DCR-2, or an antigen binding fragment thereof, for binding to the extracellular domain of CD300f, wherein the antibody, or antigen binding fragment thereof, that cross-competes with DCR-2 is not UP-D2, or an antigen binding fragment thereof.

The antibody or antigen binding fragment thereof may be coupled to a moiety. Accordingly, another aspect provides an immunoconjugate comprising:
    (a) a heavy chain variable region which comprises:
        (i) an amino acid sequence that is at least 70% identical, typically at least 75%, 80%, 85%, 90%, 95%, 96%, 97%, 98%, or 99% identical, to the amino acid sequence represented by SEQ ID NO: 1; and/or
        (ii) a complementarity determining region 1 (CDR1) comprising the amino acid sequence represented by SEQ ID NO: 2, a complementarity determining region 2 (CDR2) comprising the amino acid sequence represented by SEQ ID NO: 3, and/or a complementarity determining region 3 (CDR3) comprising the amino acid sequence represented by SEQ ID NO: 4; and/or (b) a light chain variable region which comprises:
(i) an amino acid sequence that is at least 70% identical, typically at least 75%, 80%, 85%, 90%, 95%, 96%, 97%, 98%, or 99% identical, to the amino acid sequence represented by SEQ ID NO: 5; or
(ii) a complementarity determining region 1 (CDR1) comprising the amino acid sequence represented by SEQ ID NO: 6, a complementarity determining region 2 (CDR2) comprising the amino acid sequence represented by SEQ ID NO: 7, and/or a complementarity determining region 3 (CDR3) comprising the amino acid sequence represented by SEQ ID NO: 8, wherein the antibody or antigen binding fragment thereof is coupled to a moiety.

The moiety can be directly or indirectly coupled to the antibody, or antigen binding fragment thereof (e.g., can comprise a linker in the case of indirect binding). Examples of moieties include, a radioisotope (e.g., iodine-131, yttrium-90 or indium-111), a detectable label (e.g., a fluorophore or a fluorescent nanocrystal), a therapeutic compound (e.g., a chemotherapeutic or an anti-inflammatory), a colloid (e.g., gold), a toxin (e.g., ricin), a nucleic acid, a peptide (e.g., a serum albumin binding peptide), a protein (e.g., a protein comprising an antigen binding domain of an antibody or serum albumin), a compound that increases the half-life of the antibody or antigen binding protein in a subject (e.g., polyethylene glycol or other water soluble polymer having this activity) or mixtures thereof. Methods for coupling moieties to proteins are known in the art and described in, for example, WO2010/059821.

In one embodiment, the moiety is a therapeutic moiety and/or a diagnostic moiety.

In one embodiment, the moiety is a therapeutic moiety. A therapeutic moiety is a compound, molecule or atom which is useful in the treatment of a disease or condition. Examples of therapeutic moieties include: drugs, such as cytotoxic agents, such as chemotherapeutic agents; pro-apoptotic agents; radioisotopes; immunotoxins. A cytotoxic agent is a compound which is toxic to cells. Examples of cytotoxic agents include cytochalasin B, gramicidin, emetine, tenoposide, colchicine, duocarmycins, calicheamicins, maytansines, doxorubicin, cyclophosphamide, methotrexate, mustine, vincristine, procarbzine, prednisolone, bleomycin, vinblastine, dacarbazine, cyclophosphamide, Procarbazine, Paclitaxel, Irinotecan, Gemcitabine, Fluorouracil, Cytarabine, ozogamicin, adriamycin, etoposide, melphalan, mitomycin C, chloramuil, daunorubicin, monomethyl-auristatin E (MMAE). Examples of radioisotopes include phosphorus-32, copper-67, arsenic-77, rhodium-105, palladium-109, silver-111, tin-1221, iodine-125, iodine-131, holmium-166, lutetium-177, rhenium-186, iridium-194, gold-199, astatium-211, yttrium-90, and bismuth-212. Examples of immunotoxins are described in, for example, Wayne et al. (2016) Blood, 123: 2470-2477, and include, for example, diphtheria toxin A, Ricin-dgA, Pseudomonas exotoxin A, Glonin, tetanus.

In one embodiment, the moiety is a diagnostic moiety. A diagnostic moiety is a compound, molecule or atom which is useful in the detection of binding of the antibody, or antigen binding fragment thereof, to its target antigen. A diagnostic moiety can comprise a radionuclide or non-radionuclide, a contrast agent (such as for magnetic resonance imaging, computed tomography or ultrasound). Diagnostic moieties include, for example, radioisotopes, dyes (such as with the biotin-streptavidin complex), contrast agents, fluorescent compounds or molecules and enhancing agents (e.g., paramagnetic ions) for magnetic resonance imaging (MRI) or positron emission tomography (PET) scanning. In one embodiment, the diagnostic moieties are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking.

In one embodiment, the moiety is monomethyl auristatin E (MMAE). To produce immunoconjugates in which the moiety is MMAE, a lysosomal cathepsin B cleavable, self-emolative dipeptide valine-citrulline (ValCit) maleimide linker can be linked to auristatin E for conjugation to partially reduced antibody, or antigen binding fragment thereof, as described in, for example, Francisco et al. 2003, Blood, 102: 1458-1465.

Also provided herein is a nucleic acid encoding a polypeptide which comprises a DCR-2 antibody, or a portion of the DCR-2 antibody, or an antigen binding fragment of the DCR-2 antibody. In various embodiments, the nucleic acid encodes a polypeptide which comprises:

(a) the amino acid sequence represented by SEQ ID NO: 1;
(b) the amino acid sequence represented by SEQ ID NO: 2,
(c) the amino acid sequence represented by SEQ ID NO: 3
(d) the amino acid sequence represented by SEQ ID NO: 4
(e) the amino acid sequence represented by SEQ ID NO: 5
(f) the amino acid sequence represented by SEQ ID NO: 6
(g) the amino acid sequence represented by SEQ ID NO: 7
(h) the amino acid sequence represented by SEQ ID NO: 8
(i) the amino acid sequence represented by SEQ ID NO: 2, 3 and 4;
(j) the amino acid sequence represented by SEQ ID NO: 6, 7 and 8;
(k) the amino acid sequence represented by SEQ ID NO: 2, 3, 4, 6, 7 and 8;
(l) the amino acid sequence represented by SEQ ID NO: 13;
(m) the amino acid sequence represented by SEQ ID NO: 14;

(n) the amino acid sequence represented by SEQ ID NO: 1, and the amino acid sequence represented by SEQ ID NO: 5.

In one embodiment, the nucleic acid encoding the polypeptide which comprises a DCR-2 antibody, a portion of the DCR-2 antibody, or antigen binding fragment of the DCR-2 antibody, is codon optimised for expression in a particular host. For example, the nucleic acid sequence represented by SEQ ID NO: 11 is nucleic acid encoding the heavy chain variable region of DCR-2 linked to human heavy chain constant region of anti-TNF IgG1, that is codon optimised for expression in CHO cells. The nucleic acid sequence represented by SEQ ID NO: 12 is nucleic acid encoding the light chain variable region of DCR-2 linked to human light chain constant region of anti-TNF kappa chain that is codon optimised for expression in CHO cells. Methods for codon optimisation of nucleic acid are known in the art and are described in, for example, Raab et al. (2010) Systems and Synthetic Biology, 4(3), pp. 215-225; Graf et al. (2004) Methods Mol. Med. 94:197-210.

Typically, the nucleic acid encoding a polypeptide which comprises a DCR-2 antibody, or antigen binding fragment thereof, is operably linked to one or more regulatory sequences for expression of the antibody or antigen binding fragment thereof. A "regulatory sequence" is a nucleotide sequence located upstream (5' non-coding sequences), within, or downstream (3' non-coding sequences) of a coding sequence, and which influences the transcription, RNA processing or stability, or translation of the associated coding sequence. Regulatory sequences are known in the art and may include, for example, transcriptional regulatory sequences such as promoters, enhancers, translation leader sequences, introns, and polyadenylation signal sequences. The expression "operably linked" refers to the placement of a regulatory sequence in such a manner as to influence the expression of the coding sequence. In some embodiments, regulatory or other nucleic acid sequences including, for example, 5' untranslated region, 3' untranslated regions, cap structure, poly A tail, translational initiators, sequences encoding signalling peptides, translational enhancers, transcriptional enhancers, translational terminators, transcriptional terminators, transcriptional promoters, and/or nucleic acid sequence encoding fusion peptides for isolation of the protein or targeting of the protein to a particular part of the cell, may be operably linked with the nucleic acid encoding the protein (see, for example, "Molecular Cloning: A Laboratory Manual", Sambrook et al., Cold Spring Harbor Laboratory, 3rd edition (2001)). Depending on the host cell and/or vector utilized, any one of a number of suitable regulatory elements known in the art may be used. "Coding sequence" refers to a DNA or RNA sequence that codes for a specific amino acid sequence, for example, the antibody or antigen binding fragment thereof. The coding sequence may be a chimeric coding sequence in that the nucleic acid in the coding sequence is from different genes. For example, a chimeric artificial T cell receptor may be prepared by linking coding sequence encoding an scFv to a coding sequence encoding a T cell transmembrane and endodomain, such as CD3-zeta transmembrane and endodomain. The coding sequence is typically operably linked to a promoter. A promoter is a DNA region capable under certain conditions of binding RNA polymerase and initiating transcription of a coding sequence usually located downstream (in the 3' direction) from the promoter. The coding sequence may also be operably linked to termination signals. Typically, the coding sequence is operably linked to regulatory sequences to facilitate expression of the coding sequence in an expression vector. The expression vector may also include sequences required for proper translation of the coding sequence. The coding sequence in the expression vector may be under the control of a constitutive promoter or a regulatable promoter that initiates transcription only in a particular cell types, or when the host cell is exposed to some particular stimulus. For example, in an expression vector comprising a nucleic acid encoding the antibody or antigen binding fragment thereof, the coding sequence may be operably linked to a promoter which expresses the coding sequence in, or is inducible in, various host cells. Regulatory sequences used to facilitate expression of the antibody or antigen binding fragment thereof in various host cells are known in the art.

As used herein, "expression" of a nucleic acid sequence refers to the transcription and translation of a nucleic acid sequence comprising a coding sequence to produce the polypeptide encoded by the coding sequence.

Promoters suitable for expression in bacterial cells include, for example, lacz, Ipp, a temperature-sensitive L or R promoters, T7, T3, SP6 or semi-artificial promoters such as the IPTG-inducible tac promoter or lacUV5 promoter. Promoters suitable for expression in yeast cells such as, *Pichia pastoris, Saccharomyces cerevisiae* and *S. pombe*, include, for example, promoters from the following genes ADH1, GAL1, GAL4, CUP1, PHO5, RPR1, or TEF1. Promoters suitable for expression in a mammalian cell include, for example a promoter selected from the group consisting of, retroviral LTR elements, the SV40 early promoter, the SV40 late promoter, the CMV IE (cytomegalovirus immediate early) promoter, the EF1 promoter (from human elongation factor 1), the EM7 promoter, the UbC promoter (from human ubiquitin C). Examples of useful mammalian host cell lines include monkey kidney CVI line transformed by SV40 (COS-7); human embryonic kidney line (HEK-293 cells); baby hamster kidney cells (BHK); Chinese hamster ovary cells (CHO); African green monkey kidney cells (VERO-76); or myeloma cells (e.g., NS/0 cells).

The nucleic acid encoding the polypeptide comprising the DCR-2 antibody, or antigen binding fragment thereof, is typically introduced into a host cell in a vector, such as an expression vector. As used herein, the term "vector" means any mechanism for the transfer of a nucleic acid into a host cell, either in vitro, ex vivo or in vivo. Vectors may be commercially obtained from companies such as Promega, Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, for example, transcriptional promoters, transcriptional enhancers, transcriptional terminators, translational initiators, translational, terminators, ribosome binding sites, 5' untranslated region, 3' untranslated regions, cap structure, poly A tail, origin of replication, detectable markers, affinity tags, signal or target peptide. It will be understood that the selection and/or construction of a suitable vector may depend upon several factors, including, for example, the type of cell or host cell, the type of transcriptional and translational control elements desired, the means of isolation of the protein desired, whether chromosomal integration is desired, the type of selection process that is desired.

Suitable vectors include, but are not limited to, the vectors described in the Examples, pCELF, pCELP, pcDNA3, pMC1neo, pXT1, pSG5, EBO-pSV2, pBPV-1, pBPV-MMT-neo, pRSVgpt, pRSVneo, pSV2-dhfr, pUCTag, IZD35, pHB-Apr-1-neo, EBO-pcD-XN, pcDNA1/amp, pcDNA1/neo, pRc/CMV, pSV2gpt, pSV2neo, pSV2dhfr, pTk2, pMSG, pSVT7, pKoneo and pHyg. Such vectors may contain an origin of replication for autonomous replication in host cells, selectable markers, a number of useful restriction enzyme sites, a potential for high copy number, and promoters active in a particular cell type.

Suitable host cells will depend on the nucleic acid expressed, the control elements operably linked to the nucleic acid and the purpose of the isolated protein. Suitable host cells may include mammalian cells such as, for example, CHO, HEK-293, baby hamster kidney cells (BHK), VERO-76 and myeloma cells. For expression in mammalian cells, suitable promoters are known in the art and include, for example, SV40 early promoter, SV40 late promoter, CMV promoter, EF1 promoter, and EM7 promoter.

In embodiments in which the nucleic acid is expressed in T cells for production of CART cells, the host cell may be T cells. T cells for CART may be isolated using methods known in the art, such as leukapheresis. Methods for preparing CART cells are know in the art and described in Shannon et al. (2015) Blood, 125(26): 4017-4023; O'Hear et al. (2015) Haematologica 100(3): 336-344.

Methods for producing expression vectors, for example, cloning into expression constructs/vectors are known in the art and/or described in Ausubel et al., (In: Current Protocols in Molecular Biology. Wiley Interscience, ISBN 047 150338, 1987), and (Sambrook et al., (In: Molecular Cloning: Molecular Cloning: A Laboratory Manual, Cold Spring Harbor Laboratories, New York, Third Edition 2001) and U.S. Pat. No. 7,270,969.

Expression vectors may be introduced into a suitable host cells using any methods known in the art. Suitable methods include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The cells used to express the DCR-2 antibody, or antigen binding fragment thereof, may then be cultured under conditions known in the art to express the DCR-2 antibody, or antigen binding fragment thereof.

The antibodies, or antigen binding fragments thereof, immunoconjugates, nucleic acids, and cells, described herein may be formulated as a pharmaceutical composition. Accordingly, a further aspect provides a pharmaceutical composition comprising:
  (a) an isolated DCR-2 antibody, or antigen binding fragment thereof, as described herein; or
  (b) an immunoconjugate comprising an isolated DCR-2 antibody, or antigen binding fragment thereof, as described herein coupled to a moiety, such as a therapeutic or diagnostic moiety; or
  (c) a cell comprising a nucleic acid encoding a polypeptide comprising the DCR-2 antibody, or a portion of the DCR-2 antibody, or antigen binding fragment of the DCR-2 antibody, as described herein; or
  (d) a nucleic acid encoding a polypeptide comprising a DCR-2 antibody, or portion thereof, or an antigen binding fragment of the DCR-2 antibody, as described herein.
  and a pharmaceutically acceptable carrier.

In some embodiments, the pharmaceutical composition further comprises monoclonal antibody UP-D2, or an antigen binding fragment thereof, or an immunoconjugate comprising UP-D2, or an antigen binding fragment thereof, coupled to a therapeutic and/or diagnostic moiety.

In various embodiments, the composition comprises:
  (a) the DCR-2 antibody, or an antigen binding fragment thereof, as described herein;
  (b) the DCR-2 antibody, or antigen binding fragment thereof, as described herein and the UP-D2 antibody, or an antigen binding fragment thereof;
  (c) an immunoconjugate comprising the DCR-2 antibody, or antigen binding fragment thereof, as described herein;
  (d) an immunoconjugate comprising the DCR-2 antibody, or antigen binding fragment thereof, as described herein, and the UP-D2 antibody, or an antigen binding fragment thereof;
  (e) the DCR-2 antibody, or antigen binding fragment thereof, as described herein, and an immunoconjugate comprising the UP-D2 antibody, or an antigen binding fragment thereof; or
  (f) an immunoconjugate comprising the DCR-2 antibody, or antigen binding fragment thereof, as described herein, and an immunoconjugate comprising the UP-D2 antibody, or an antigen binding fragment thereof, and a pharmaceutically acceptable carrier.

A "pharmaceutically acceptable carrier" means that it is compatible with the other ingredients of the composition and is not deleterious to a subject. The compositions may contain other therapeutic agents as described below, and may be formulated, for example, by employing conventional liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

The pharmaceutical compositions are typically in the form of a sterile injectable aqueous suspension. This suspension may be formulated according to the known art and contain the active materials in admixture with excipients suitable for the manufacture of aqueous suspensions. Such excipients may include suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

As described in the Examples, the inventors have found that DCR-2 binds to cells expressing CD300f, including AML and leukaemic stem cells. Although the use of DCR-2 has been described in the context of myeloid leukaemias such as AML, it will be appreciate by those skilled in the art that the DCR-2 antibody, or antigen binding fragments thereof, as described herein, may also be used to treat other conditions associated with CD300f expression.

Accordingly, the DCR-2 antibody, or antigen binding fragment thereof, described herein may be used to treat a subject suffering from a condition associated with CD300f expression. Accordingly, a further aspect provides a method of treating a condition associated with CD300f expression, such as AML, comprising administering to a subject in need thereof an effective amount of an antibody, or antigen binding fragment thereof, that specifically binds CD300f, or an immunoconjugate thereof, wherein the antibody, antigen binding fragment thereof, comprises:
  (a) a heavy chain variable region which comprises:
    (i) an amino acid sequence that is at least 70% identical, typically at least 75%, 80%, 85%, 90%, 95%, 96%, 97%, 98%, or 99% identical to the amino acid sequence represented by SEQ ID NO: 1; and/or
    (ii) a complementarity determining region 1 (CDR1) comprising the amino acid sequence represented by SEQ ID NO: 2, a complementarity determining region 2 (CDR2) comprising the amino acid sequence represented by SEQ ID NO: 3, and/or a complementarity determining region 3 (CDR3) comprising the amino acid sequence represented by SEQ ID NO: 4; and/or
  (b) a light chain variable region which comprises:
    (i) an amino acid sequence that is at least 70% identical, 70%, typically at least 75%, 80%, 85%, 90%, 95%, 96%, 97%, 98%, or 99% identical to the amino acid sequence represented by SEQ ID NO: 5; and/or
    (ii) a complementarity determining region 1 (CDR1) comprising the amino acid sequence represented by SEQ ID NO: 6, a complementarity determining region 2 (CDR2) comprising the amino acid sequence represented by SEQ ID NO: 7, and/or a complementarity determining region 3 (CDR3) comprising the amino acid sequence represented by SEQ ID NO: 8.

Typically, the condition is a myeloid leukaemia. Typically, the myeloid leukaemia is AML.

In one embodiment, the method further comprises administering to the subject monoclonal antibody UP-D2, or an antigen binding fragment or derivative thereof, or an immunoconjugate comprising UP-D2 or an antigen binding fragment or derivative thereof linked to a moiety, typically a therapeutic moiety.

In various embodiments, there is provided a method of treating a condition associated with CD300f expression, such as AML, comprising administering to a subject in need thereof an effective amount of:
  (a) the DCR-2 antibody, or an antigen binding fragment thereof, as described herein;
  (b) the DCR-2 antibody, or antigen binding fragment thereof, as described herein, and the UP-D2 antibody or an antigen binding fragment thereof described herein;
  (c) an immunoconjugate comprising the DCR-2 antibody, or antigen binding fragment thereof, as described herein, coupled to a therapeutic moiety;
  (d) a cell comprising a nucleic acid encoding a polypeptide comprising the DCR-2 antibody, or portion thereof or antigen binding fragment thereof, as described herein;
  (e) an immunoconjugate comprising the DCR-2 antibody, or antigen binding fragment thereof, as described herein, coupled to a therapeutic moiety, and the UP-D2 antibody, or an antigen binding fragment thereof, as described herein; or
  (f) an immunoconjugate comprising the DCR-2 antibody, or antigen binding fragment thereof, as described herein, coupled to a therapeutic moiety, and an immunoconjugate comprising the UP-D2 antibody, or an antigen binding fragment thereof, as described herein, coupled to a therapeutic moiety.

Typically, the antibody, antigen binding fragment thereof are administered in a pharmaceutically acceptance composition as described herein.

The pharmaceutical composition may be administered by any suitable means, typically, parenterally, such as by subcutaneous, intravenous, intramuscular, intra(trans)dermal, or intracisternal injection or infusion techniques (e.g., as sterile injectable aqueous solutions or suspensions); in dosage unit formulations containing non-toxic, pharmaceutically acceptable vehicles or diluents. The antibody or antigen binding fragment thereof may, for example, be administered in a form suitable for immediate release or extended release: Immediate release or extended release may be achieved by the use of suitable pharmaceutical compositions comprising the compounds, or, particularly in the case of extended release, by the use of devices such as subcutaneous implants or osmotic pumps.

The pharmaceutical compositions for the administration may conveniently be presented in dosage unit form and may be prepared by any of the methods well known in the art of pharmacy. In general, the pharmaceutical compositions are prepared by uniformly and intimately bringing the compound into association with a liquid carrier. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Generally, the term "treating" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease. In one embodiment, treatment achieves the result of reducing the number of CD300f expressing cells, such as AML and/or LSC cells, in the recipient subject.

The term "subject" refers to any animal having a disease which requires treatment by the present method. In addition to primates, such as humans, a variety of other mammals can be treated using the methods of the present invention. For instance, mammals including, but not limited to, cows, sheep, goats, horses, dogs, cats, guinea pigs, rats or other bovine, ovine, equine, canine, feline, rodent or murine species can be treated. Dogs in particular are known to experience multiple myeloma.

The term "therapeutically effective amount" refers to the amount of the antibody, antigen binding fragment or immunoconjugate that will elicit the biological or medical response of a tissue, system, animal or human that is being sought by the researcher, veterinarian, medical doctor or other clinician.

In the treatment or prevention of AML, an appropriate dosage level will generally be about 0.01 to 50 mg per kg patient body weight per day which can be administered in single or multiple doses. Preferably, the dosage level will be about 0.1 to about 25 mg/kg per day; more preferably about 0.5 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.05 to 0.5, 0.5 to 5 or mg/kg per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also disclosed herein is a kit comprising the DCR-2 antibody, or antigen binding fragment thereof, described herein, typically comprising one or more containers filled with antibody, or antigen bind fragment thereof, for the treatment of a condition associated with CD300f expression, such as AML. In various embodiments, the kit comprises:
  (a) the DCR-2 antibody, or an antigen binding fragment thereof, as described herein;
  (b) the DCR-2 antibody, or antigen binding fragment thereof, as described herein, and the UP-D2 antibody, or an antigen binding fragment thereof, described herein;
  (c) an immunoconjugate comprising the DCR-2 antibody, or antigen binding fragment thereof, as described herein coupled to a therapeutic moiety;
  (d) a cell comprising a nucleic acid encoding a polypeptide comprising the DCR-2 antibody, or portion thereof, or an antigen binding fragment thereof, as described herein;
  (e) an immunoconjugate comprising the DCR-2 antibody, or antigen binding fragment thereof, as described herein, coupled to a therapeutic moiety, and the UP-D2 antibody, or an antigen binding fragment thereof, as described herein; or
  (f) an immunoconjugate comprising the DCR-2 antibody, or antigen binding fragment thereof, as described herein, coupled to a therapeutic moiety, and an immunoconjugate comprising the UP-D2 antibody, or an antigen binding fragment thereof, as described herein, coupled to a therapeutic moiety,
in one or more containers. In another embodiment, the kit comprises the DCR-2 antibody, or antigen bind fragment thereof, described herein, in one or more containers, and one or more other therapeutic agents useful for the treatment of a condition associated with CD300f expression, such as AML. In another embodiment, the kit comprises the DCR-2 antibody, or antigen bind fragment thereof, described herein, in one or more containers, and one or more other diagnostic agents. A further embodiment provides a kit comprising DCR-2 antibody, or antigen bind fragment thereof, described herein, and the UP-D2 antibody, or antigen bind fragment or derivative thereof for the treatment of a condition associated with CD300f expression, such as AML.

It is to be understood that the terminology used herein is for the purpose of describing particular embodiments only, and is not intended to limit the scope of the present invention which will be limited only by the appended claims. As used herein and in the appended claims, the singular forms "a", "an", and "the" include plural reference unless the context clearly indicates otherwise. Thus, for example, a reference to "an antibody" includes a plurality of such antibodies. Unless defined otherwise, all technical and scientific terms used herein have the same meaning as commonly understood by one of ordinary skill in the art to which this invention belongs. Although any materials and methods similar or equivalent to those described herein can be used to practice or test the present invention, preferred materials and methods are described herein.

All publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

All publications mentioned in this specification are herein incorporated by reference. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In order to exemplify the nature of the present invention such that it may be more clearly understood, the following non-limiting examples are provided.

EXAMPLES

Methods
Antibodies

Monoclonal antibody DCR-2 (IgG1, κ) was generated from splenocytes collected from a mouse immunised with CD300f expressing CHO transfectants which had been transfected with a recombinant form of CD300f Ig domain, and boosted with recombinant CD300f-Fc protein (Sino Biologicals). The splenocytes were fused to the NS-1 myeloma cell line.

The resulting hybridoma, which expresses DCR-2, was deposited under the Budapest Treaty at CellBank Australia, 214 Hawkesbury Rd., Westmead, NSW 2145, Australia, on 27 Sep. 2016 and designated accession number CBA20160029. Commercially available CD300f antibodies that were used in this study were monoclonal antibodies UP-D1 (mouse IgG1, κ, EF660 conjugate, Jomar Life Research, Victoria, Australia), UP-D2 (mouse IgG1, κ, PE conjugate and purified, Biolegend, CA, USA), and 234903 (rat IgG2b, R&D Systems, MN, USA), and the polyclonal manufacturer's recommendations (GE Healthcare Life Sciences). Mononuclear blasts were prepared from excess AML diagnostic samples. Table 2 summarizes the characteristics of AML samples. The CRGH Human Ethics Committee approved all protocols.

TABLE 2

| Sample ID | Sample | WHO Diagnosis | Fab | WCC | BM blasts % | Karyotype | NPM1 | FLT3 |
|---|---|---|---|---|---|---|---|---|
| 1 | PB | AML with MDS changes | M2 | 128 | 55 | Normal | ND | ND |
| 2 | BM | AML NOS | M4 | 14.1 | 70 | Normal | ND | ND |
| 3 | PB | AML NOS | M2 | 15.5 | 43 | +8 | ND | ND |
| 4 | BM | Therapy related myeloid neoplasm | M4 | 16.4 | 82 | Normal | Detected | Detected |
| 5 | PB | Therapy related myeloid neoplasm | M4 | 150 | 67 | 46, XY, add(12)(q24.3) | ND | ND |
| 6 | PB | AML with MDS changes | M2 | 30.1 | 16 | Normal | ND | ND |
| 7 | PB | RAEB-2 | N/A | 3.5 | 15 | +8 | ND | ND |
| 8 | PB | AML NOS | M5 | 146 | 95 | Normal | ND | ND |
| 9 | PB | AML NOS | M0 | 2.5 | 73 | No metaphases | Negative | Negative |
| 10 | PB | AML with MDS changes | M4 | 54.3 | 56 | Normal | Negative | Detected |
| 11 | PB | CMML-2 | N/A | 5.7 | 10 | Normal | ND | ND |
| 12 | PB | AML NOS | M1 | 23.2 | ND | unknown | ND | ND |
| 13 | PB | AML with MDS changes | M5 | 62.7 | | unknown | ND | ND |
| 14 | PB | AML with MDS changes | M5 | 3.8 | 53 | +19 | ND | ND |
| 15 | BM | AML NOS | M6 | 0.7 | 26 | complex | ND | ND |
| 16 | BM | AML + inversion 16 | M4Eo | 111.3 | 45 | Inversion 16 | ND | ND |
| 17 | BM | AML NOS | M5 | 5.2 | 78 | complex | ND | Negative |
| 18 | PB | AML with MDS changes | M2 | 65 | 60 | Normal | ND | ND |
| 19 | PB | AML NOS | M0 | 8 | 85 | Normal | Detected | Negative |
| 20 | PB | AML with MDS changes | M5 | 30.1 | 80 | Complex; del(12)(p12), del(13)(q21), add(17)(p11.2) [1] 46,XX[1] | ND | ND |
| 21 | BM | AML NOS | M0 | 14.1 | 60 | Normal | Negative | Negative |
| 22 | BM | AML + inversion 16 | M4Eo | 160 | 60 | 46, XY, inv(16)(p13; q22) | Negative | Negative |
| 23 | PB | Therapy related myeloid neoplasm | M2 | 2.2 | 62 | 47, XY, t(8; 16)(p11; p13), +8 | ND | ND |
| 24 | PB | AML NOS | M5 | 64 | 90 | t(11; 17), +8 | Negative | Negative |
| 25 | PB | AML + inversion 16 | M4Eo | 34.9 | 50 | Inversion 16 | Negative | Negative |
| 26 | BM | AML NOS | M2 | 54.6 | 60 | +6 | Negative | Negative |
| 27 | BM + PB | Blastic pDC Neoplasm | N/A | 4.3 | 85 | Normal | Negative | Negative |
| 28 | BM | AML NOS | M2 | 7 | 25 | No metaphases | ND | ND |
| 29 | BM | AML NOS | M1 | | | t(9:11) | ND | ND |
| 30 | BM | AML + inversion 16 | M4Eo | | | inv 16 | ND | ND |
| 31 | BM | AML NOS | M4 | | | +8 | ND | ND |
| 32 | BM | AML NOS | M2 | | | monosomy 7 | ND | ND |
| 33 | BM | AML NOS | M4 | | | Normal | ND | ND |
| 34 | PB | AML NOS | M4 | 10.0 | 85 | Normal | Negative | Negative |

ND; not determined antibodies used were rabbit antibody to CLM-1 (CLM-1, N-Terminal 63-92, Abcam, Cambridge, UK) and goat anti-human LMIR3 (gLMIR3, R&D Systems, MN, USA).

The following antibodies were also used: CD45 V500 (clone HI30), CD34 PE-CY7 (clone 581), CD38 V450 (clone HB7) and propidum iodide to determine viability obtained from BD Biosciences; CD141 (PE) and CD304 (APC) from Miltenyi Biotech; from R&D Systems.

Cell Lines

The myeloid derived cell lines HEL, HL-60, U937 and THP-1 (all from ATCC) were grown in complete RPMI containing 200 mM glutaMAX (ThermoFisher), 100 U/ml Penicillin/100 µg/ml Streptomycin (ThermoFisher) and 10% heat inactivated fetal bovine serum.

Human Samples

Venous and bone marrow samples were obtained, with informed consent, from healthy volunteers collected through the Department of Hematology, Concord Repatriation General Hospital (CRGH). Mononuclear cells were prepared using Ficoll-Paque density gradient centrifugation using the $CD14^+$ monocytes were purified from PBMC labelled with CD14 mAb (clone M5E2, BD Biosciences) directly conjugated FITC and purified by cytometric sorting on a BD Influx. AML samples were phenotyped with the following mAbs from BD Biosciences: CD45-V500 (clone HI30), CD34-PE-CY7 (clone 581), CD38-V450 (clone HB7) and CD33-PE (clone WM53). Results were analyzed with FlowJo (Treestar). After initially gating on PI negative viable cells, hematopoietic stem cells were identified as lineage-CD45dimCD34+CD38-CD45RA-CD90+. Blasts were identified as CD45dimSSClow. The leukemia stem cell enriched CD34+CD38− fraction was identified from this gate.

Propidium iodide (PI) was used to determine viability. AML blasts were purified from peripheral blood or bone marrow AML samples labelled with CD45-V500 (BD Biosciences) by cytometric sorting for the $SSC^{Lo}CD45^{dim}$ population.

Generation of CD300f Transfectants

Full length CD300f cDNA (Isoform 1) containing a c-myc epitope located after the leader sequence was cloned into the CMV promoter of the pBud vector. CHO cells were transfected with the constructs using Lipofectamine 3000 and selected with zeocin to generate stable transfectants. Cells expressing surface c-myc were sorted on a BD Influx. CD300a, CD300f$^{L4}$ and CD300f$^{S4}$ were similarly expressed in CHO cells. All constructs were validated by sequencing at the Australian Research Genome Facility.

Flow Cytometry

Cells were stained according to standard protocols with directly conjugated specific, or isotype control, antibodies to discriminate between different populations. Briefly, cells were incubated for 20 min at 4° C. with mAb diluted in PBS/0.5% BSA. Unlabeled mouse antibodies were detected with a second incubation with a species specific Alexafluor (AF)488 F(ab)$_2$ reagent (goat anti-mouse, goat anti-rat or rabbit anti-goat, or donkey anti-rabbit, Invitrogen). Live and dead cell events were identified as Propidium Iodide events. Cells were analyzed on either an Accuri C6, Fortessa LSR or Influx (both from BD Biosciences).

Blocking experiments were performed by pre-incubating 10$^5$ CD300f-CHO cells with the blocking antibody at 50% saturation concentration in 0.5% BSA/PBS for 30 mins on ice. The cells were washed with 0.5% BSA/PBS before incubation with directly labelled test antibody. Experiments were repeated three times Percent binding was determined from geometric mean fluorescence intensity (MFI) by [MFI Blocked Antibody-MFI Unblocked Isotype]/[Unblocked Antibody-Isotype control]×100.

ELISA

The specificity of each antibody for the CD300f Ig domain was confirmed by ELISA. Maxisorp plates were coated with goat anti-human Ig Fc (Sigma) in carbonate buffer, blocked with 5% BSA/PBS before capturing CD300f-Ig, CD300b-Ig or control recombinant fusion protein (Sino). Each antibody and appropriate species and isotype controls were then incubated with the captured fusion protein (or control) and their binding was detected with an appropriate HRP labelled secondary antibody and OPD.

Immunoprecipitation and Western Blots

For immunoprecipitation, 2.5×10$^7$ cells were biotinylated with Sulfo-NHS-Biotin (ThermoFisher) lysates before lysis in M-PER buffer. Proteins were immunoprecipitated with antibodies bound to Protein G Dynal beads according to the manufacturer's recommendations (Thermofisher). Immunoprecipitated proteins or M-PER lysates were separated on a 4-12% Bis-Tris Plus gel (Invitrogen) without or with anti-oxidant (for reducing condition) and transferred to nitrocellulose using an iBlot system (Thermo). Membranes were blocked with 5% BSA/TTBS, were incubated with primary antibody, followed by HRP-conjugated species specific antibody, detected with Enhanced chemiluminescence (ECL) reagent (Clarity ECL kit, Bio Rad) and analysed using a BioRad Chemidoc imaging system. Biotinylated protein was detected with Strepavidin-HRP and ECL.

Gene Expression Analysis

Total RNA was prepared from freshly purified cell populations or cells growing in exponential growth phase using TRIzol Reagent as per manufacturer's instructions (Thermo Fisher). Integrity and quantity of extracted mRNA was assessed using an RNA 6000 Nano Bioanalyzer (Agilent Technologies). All RNA used had an RNA Integrity Number (RIN) greater than 8.8. For cDNA, 100 ng of DNase I (Thermo Fisher) treated RNA was reverse transcribed into cDNA using the SuperScript III kit (Thermo Fisher). Hydrolysis probes were designed to detect splice variants and checked for specificity by a BLAST alignment. Gene expression was performed on the cDNA using 300 mM primers, 300 mM Fam BHQuencher labelled probes (EBiosearch) and 1× Fast TAQMAN® Master Mix (Thermo Fisher). Duplicate samples of cDNA were amplified on a 7500 Fast Real-time PCR system (Thermo Fisher). CT values for splice variant amplification were normalized to the UBC endogenous gene and presented as fold changes to a CD14$^+$ cDNA reference sample using the formula: fold change=2-ΔΔCT(11). Primer efficiencies of all primer pairs were greater than 98%. The primer and probe sequences were L5-L1 (detecting isoforms 1, 3, 4, 7):

(SEQ ID NO: 16)
5'TACCTGCTCCTCTTCTG;

L5-R1-
(SEQ ID NO: 17)
5'CCAAGCCATTCACTGTT;

L5-P1:
(SEQ ID NO: 18)
5'TCTCAGGCTACTCCATTGTCACTCA$^{FAM-BHQ}$;

L5-SV1-1 (detecting isoforms 1, 4, 5):
(SEQ ID NO: 19)
5'CTTGGGTGCTGAGGAT;

L5-SV1-2:
(SEQ ID NO: 20)
5'AGGTGGCTACTGAGGT;

L5-SV1-P:
(SEQ ID NO: 21)
5'CAGGAACCGACCTACTGCAACATG$^{FAM-BHQ}$;

X5-3-FSP (detecting isoform 2:
(SEQ ID NO 22)
5'CACCAGTCACCCAAGAAGAAACTAG;

X5-3'-RSP:
(SEQ ID NO: 23)
5'CATCCCGGCTGCTGTTGTC;

X5-3'-Probe:

| | |
|---|---|
| 5'CCAACTCTGACCGGCCACCA<sup>FAM-BHQ</sup>; | (SEQ ID NO: 24) |

X4-3'-FSP (detecting isoforms 1, 4, 5):

5'GTGGCCGCCTCACTCTTG;    (SEQ ID NO: 25)

X4-3'-RSP:

5'GGGTCAGGTCTGCATAGCA;    (SEQ ID NO: 26)

X4-3'-Probe:

5'TTGGAGGATGATGAAGTACCAGCAGA<sup>FAM-BHQ</sup>;    (SEQ ID NO: 27)

X3-3'-FSP (detecting isoform 3):

5'GTCACCCAAGAAGAAACTAGCA;    (SEQ ID NO: 28)

X3-3'-RSP:

5'GGAACCCTCACTCCTGTTGTC;    (SEQ ID NO: 29)

X3-3'-Probe:

5'CCAACTCTGACCGGCCACCA<sup>FAM-BHQ</sup>;    (SEQ ID NO: 30)

X2-5'-FSP (detecting isoform 2, 5, 6):

5'GCCTCTCCACAGCCATCTG;    (SEQ ID NO: 31)

X2-5'-RSP:

5'GGAGTAGCCTTGACTCTTAGCA;    (SEQ ID NO: 32)

X2-5'-Probe:

5'ATGTGGCTGCCTCAGCTCGACCT<sup>FAM-BHQ</sup>;    (SEQ ID NO: 33)

UBC-F:

5'TGAAGAGAATCCACAAGGAATTGA;    (SEQ ID NO: 34)

UBC-R:

5'CAACAGGACCTGCTGAACACTG;
and    (SEQ ID NO: 35)

UBC-Probe

5'TGATCTGGCACGGGACCCTCCA<sup>FAM-BHQ</sup>.    (SEQ ID NO: 36)

Primers used to amplify and clone full length sequences were
CD300f_For_164:

GCAGAAGCTTGGGTACCTGTAGTTTGTTCC;    (SEQ ID NO: 37)

CD300f Rev:

TATCTCGAGATTCTAGAAGGCCTGCTGTAGGT    (SEQ ID NO: 38)
and

X2-5'-FSP.

Antibody Dependent Cell Cytotoxicity

C57BL/6 splenocytes were cultured with calcein labelled HL-60 cells at indicated effector:target ratios in complete RPMI containing 100 U/ml human IL-2. The cultures included 20 μg/ml CD300f or isotype control mAb. The percentage of dead HL-60 cells (DAPI+calcein−) was determined after 20 hrs culture by flow cytometry.

Internalisation of CD300f

Internalisation of antibody was measured by flow cytometry. Cells were labelled with CD300f mAb for 30 mins on ice before incubation at 3TC (or ice for control), then washed in PBS/0.5% BSA/0.02% azide. Remaining antibody on the cell surface was detected with AF488 or AF647 conjugated goat anti-mouse IgG(Fab')$_2$ (Thermo Scientific). Internalisation was measured as geoMFI [labelled mAb-isotype] at 37° C./geoMFI [labelled mAb-isotype] on ice with azide. The ratio of internalisation of directly labelled conjugate to surface AF488 gave an indication of the % of CD300f on the cell surface following internalisation. For confocal microscopy, cells were incubated with purified gLMIR3 antibody for 1 hour at 4° C. and then washed to remove excess antibody before being incubated at 3TC. Cells were centrifuged onto microscope slides in a Shandon cytospin, fixed in acetone and then stained with rabbit anti-goat IgG-AF488. Controls in which cells were cytospun and fixed prior to labelling were included to demonstrate membrane staining prior to internalisation.

Cells were visualized using a Leica TCS SP8×confocal microscope and a ×63 oil immersion objective. Images were processed with ImageJ software (National Institutes of Health).

Sequencing of DCR-2

Total mRNA was isolated from hybridoma expressing DCR2 (accession number CBA20160029) using TRIzol method according to manufacturer's instructions, and the isolated mRNA was reverse transcribed into cDNA. The resulting cDNA was used as a template for PCR amplication of the $V_L$ region using the primers described in Krebber et al. Reliable cloning of functional antibody variable domains from hybridomas and spleen cell repertoires employing a reengineered phage display system. 1997. *J Immunol Methods*. 201: 35. These primers enable the amplification of $V_L$ sequence from DCR-2 cDNA.

To obtain the sequence of the $V_H$ region, purified DCR-2 monoclonal antibody protein underwent tryptic digestion followed by mass spectrophotometry analysis. From the peptides identified using mass spectrometry, we identified a peptide EVKLVESGGGLVQPGGSLR (SEQ ID NO: 39) that corresponded to the FR1 region of the $V_H$ sequence of DCR-2 using MASCOT. This peptide was therefore used as the basis to prepare primers based on published primers from Essono, S. et al. A general method allowing the design of oligonucleotide primers to amplify the variable regions from immunoglobulin cDNA. 2003. J Immuno/Methods. 279: 251, that would be expected to amplify the sequence. We were able to amplify a $V_H$ region from the DCR-2 cDNA based on these primers.

The primer set that was used to amplify the $V_H$ region of DCR-2 was as follows:

```
                                    (SEQ ID NO: 40)
5'-GAGGTGAAGCTGRTGGARTCTGG-3'
``` wherein:

R is G or A.

The $V_H$ and $V_L$ PCR amplification products were cloned into vector pCR-BLUNT (Thermo Fisher Scientific) and the nucleic acid sequence was determined by Sanger Sequencing at the Australian Genome Research Facility (AGRF), at the Westmead Institute for Medical Research. The amino acid sequence of $V_H$ region is shown in SEQ ID NO: 1. The amino acid sequence of the amplified $V_L$ region is shown in SEQ ID NO: 5.

The DCR-2 heavy chain joining region has the sequence GQGTLVTV.

The DCR-2 light chain sequence which overlaps with the constant region has the sequence TKLEIKR.

The $V_H$ and $V_L$ sequences were used to generate a chimeric mAb sequence by in silico combination with the sequences of a human anti-TNP kappa and anti-TNP heavy IgG1 heavy chain. Codon optimisation for expression in ExpiCHO cells (ThermoFisher Scientific) was completed through the GeneArt website, GeneOptimizer™ sequence optimization (ThermoFisher Scientific) (Raab et al. (2010) Systems and Synthetic Biology, 4(3), pp. 215-225; Graf et al. (2004) Methods Mol. Med. 94:197-210). The nucleotide sequence and amino acid sequence of the codon optimized combination of the $V_H$ region of DCR-2 and the constant region of the human anti-TNP heavy IgG1 heavy chain are shown in SEQ ID NOs: 11 and 13, respectively.

The nucleotide sequence and amino acid sequence of the codon optimized combination of the $V_L$ region of DCR-2 and the constant region of the human anti-TNP kappa chain are shown in SEQ ID NOs: 12 and 14, respectively.

Results

Figure 2:
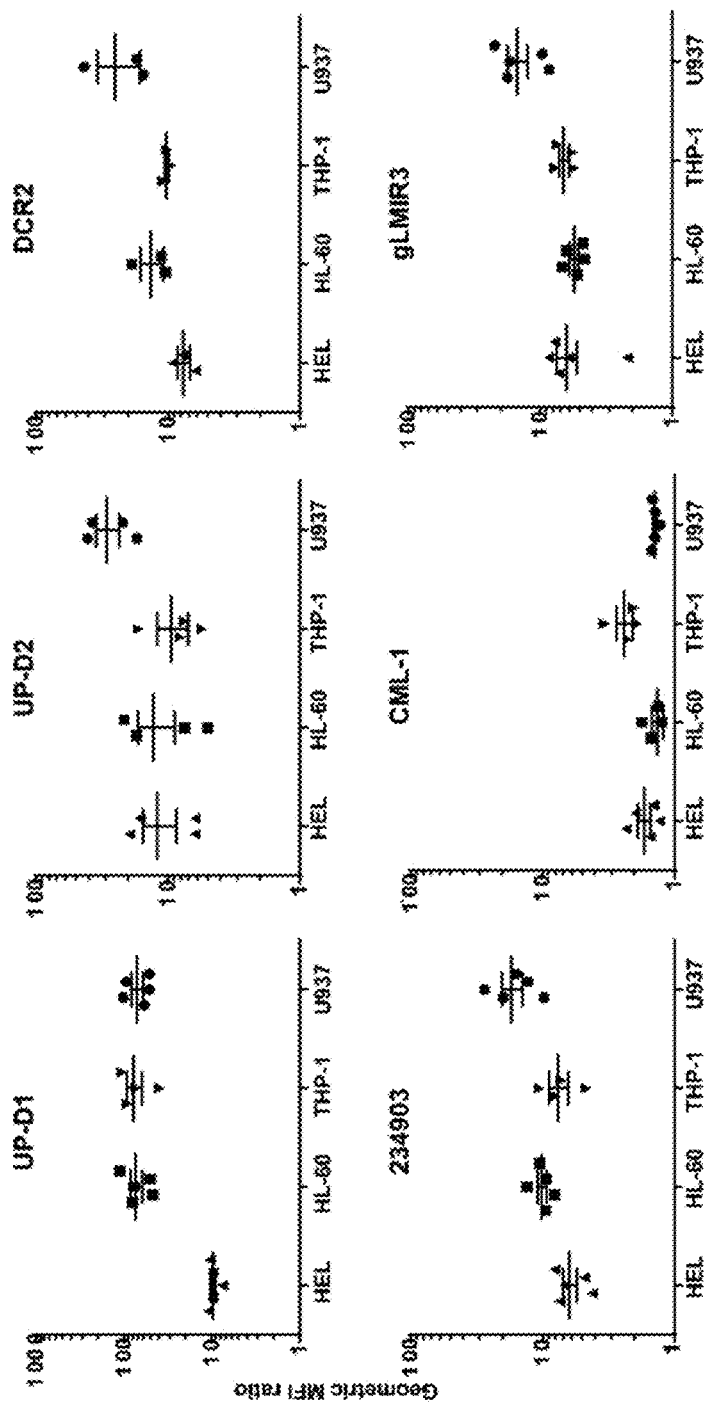
FIG. 2 are graphs showing the geometric MFI ratio for binding of DCR-2 and commercial antibodies (UP-D1, UP-D2, 234903, CML-1 and gLMIR3) to myeloid derived cells lines HEL, HL-60, THP-1 and U937. ELISA was performed n=2, error bars represent SEM from duplicate wells of representative result.
Figure 3:
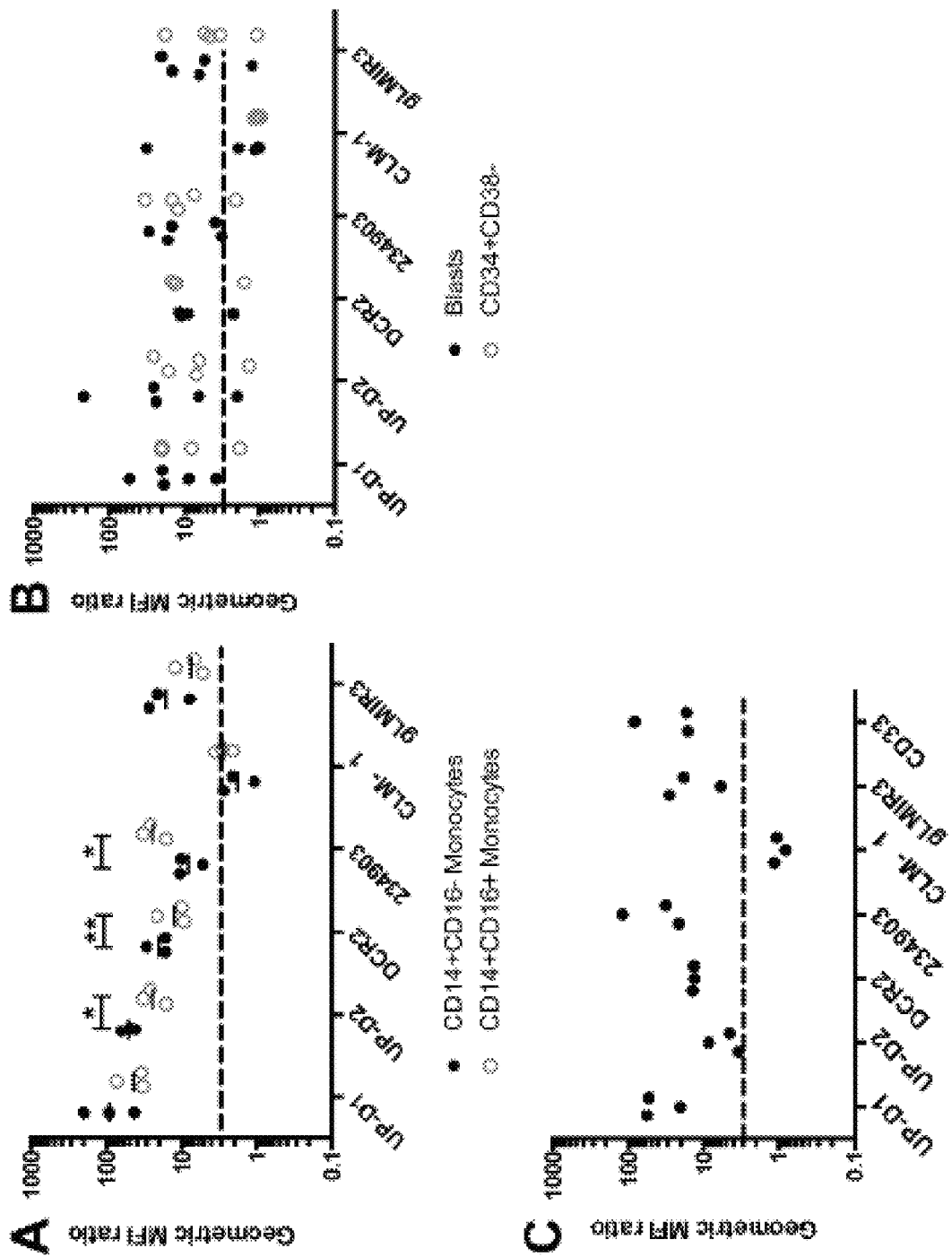
FIGS. 3A-3C are graphs showing the binding of CD300f antibodies to healthy and leukemic cells.

Validation of a panel of CD300f antibodies. We assembled a panel of antibodies to compare with DCR-2 as described in the methods. Each antibody bound to CHO transfectant cell surface CD300f transcribed from a construct encoding Isoform 1 (Accession number; NP_620587) (FIG. 1A). The CD300 family includes other molecules encoded by independent genes (CD300a, CD300b, CD300c, CD300d, CD300e) expressed on leucocytes. Because these share significant amino acid sequence similarity in the Ig domain with CD300f, we determined the binding of DCR-2 and other CD300f antibodies to other CD300 family members. First, we checked its binding to CHO transfectant cell surface CD300a, which is the other inhibitory family member. Neither DCR-2, nor any of the other antibodies in the panel, bound to CD300a transfected cells (data not shown). As the CD300f and CD300b Ig like domains are 75% identical, we assessed the binding in ELISA of each antibody compared to a relevant species control, to the CD300f Ig-like domain (FIG. 1B) and the CD300b Ig-like domain (FIG. 1C). The DCR-2, UP-D1, UP-D2 and 234903 mAb were specific for CD300f Ig-like domain but both the CLM-1 peptide antibody and the gLMIR3 antibody bound the Ig domain of the related CD300b molecule. Each antibody bound to the four CD300f$^+$ CD300b$^-$ myeloid derived cell lines tested Hel, HL-60, THP-1 and U937), with the exception of the CLM-1 antibody, which only bound to THP-1 (FIG. 2). When we compared the flow cytometry MFI ratio (geoMFI of specific mAb at saturation/geoMFI of species isotype), we observed different patterns for each mAb. UP-D1 had a high geoMFI binding to U937, HL-60, and THP-1 but a low ratio to HEL (FIG. 2). The 234903 clone and DCR-2 mAbs had similar binding patterns to each other with a high geoMFI ratio to U937, lower ratio binding to HL-60 and THP-1 and an even lower ratio binding to HEL. The mouse UP-D2 clone and gLMIR3 polyclonal showed similar geoMFI patterns. This data suggested the presence of at least four CD300f epitopes recognized by the antibody panel. DCR-2 and the other antibodies were tested on the CD300f$^+$ monocyte populations in healthy PBMC (FIG. 3A). The four mAbs and gLMIR3 antibody bound to both CD14$^+$CD16$^-$ (conventional) and CD14$^{dim}$CD16+(inflammatory) monocytes. The CLM-1 antibody did not bind to either monocyte population. Interestingly, the UP-D2 and DCR-2 clones bound to CD14$^+$CD16$^-$ monocytes with significantly greater intensity than to the CD14$^{lo}$CD16$^+$ monocyte population (FIG. 3A). This pattern was reversed with the 234903 mAb, which bound to the CD14$^{lo}$CD16$^+$ monocyte population with significantly greater intensity (FIG. 3A). We tested the four mAbs and two polyclonal antibodies on five representative AML samples. All antibodies bound both AML blasts and LSCs with the exception of the CLM-1 antibody, which bound the blasts from only one sample (FIG. 3B). The UP-D1, DCR-2 and 234903 mAb bound to HSC from healthy cord blood (FIG. 3C). There was weak binding of UP-D2 and no binding with the CLM-1 antibody to healthy HSC (FIG. 3C).

Figure 4:
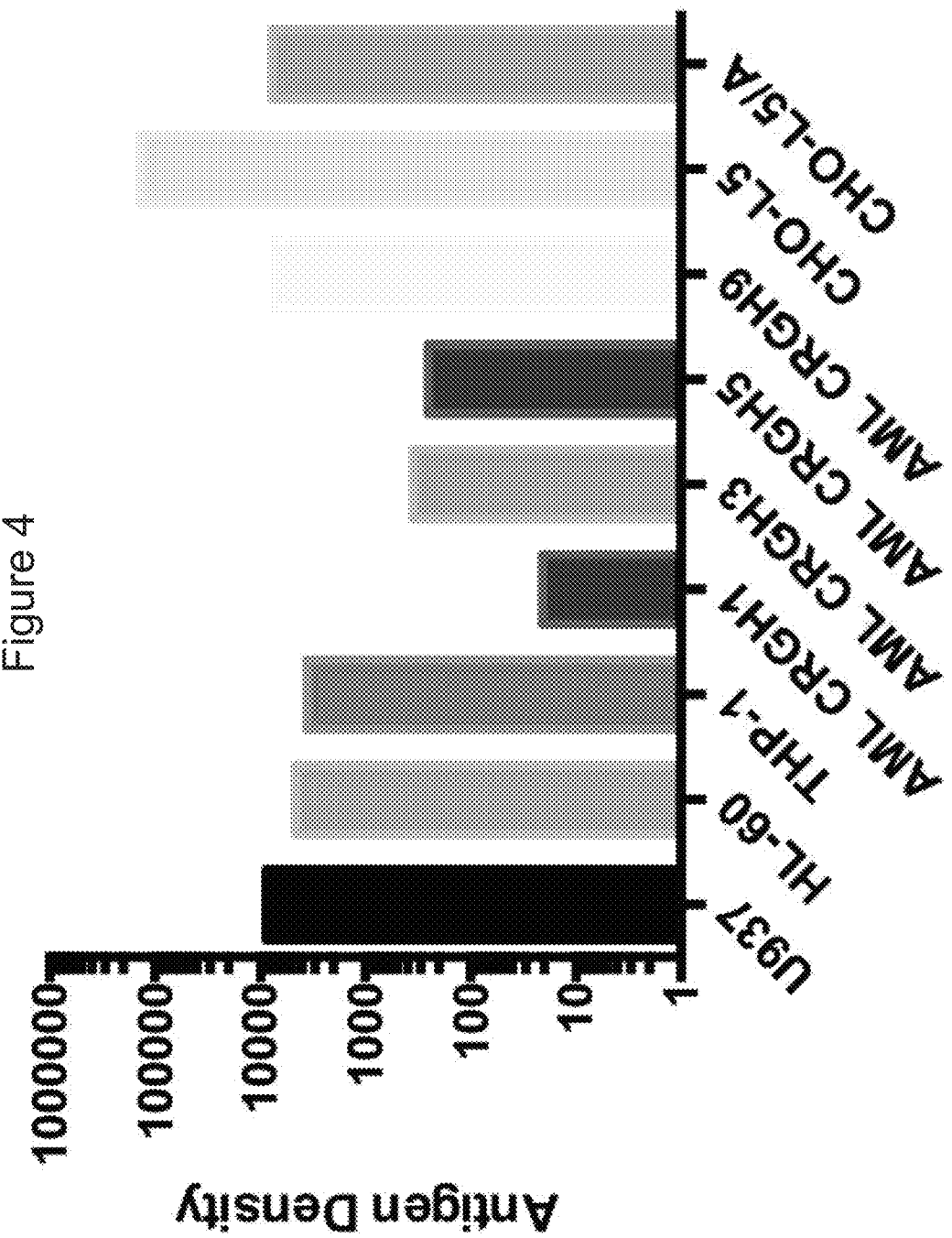
FIG. 4 is a graph showing the antigen density of CD300f on various cells detected using mAb UP-D2.

Antigen density of CD300f on the surface of myeloid derived cell lines and a number of primary AML samples with a high percentage of blasts was tested using a quantitative bead based kit. The results are shown in FIG. 4. The CD300f isoform 1 CHO transfectants expressed 10$^5$ molecules/cell. The myeloid derived cell lines expressed in the order of $10^4$ molecules per cell. Primary AML blasts expressed CD300f at levels ranging from $10^1$ to $10^4$ molecules/cell.

Figure 5:
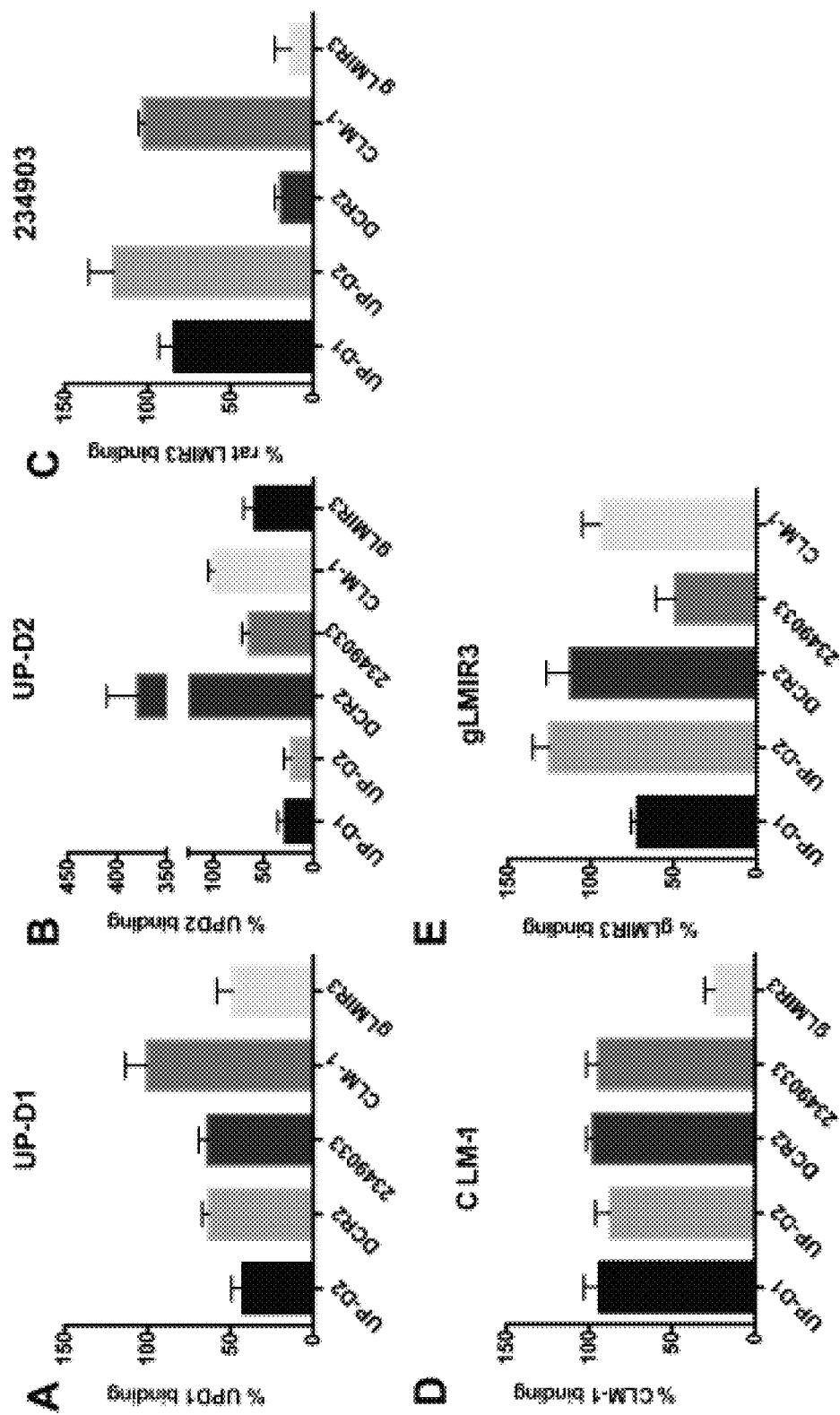
FIGS. 5A-5E are graphs showing the results of competition studies with CD300f antibodies DCR-2, UP-D1, UP-D2, 234903, CML-1 and gLMIR3. CD300f transfected CHO cells were incubated with a saturating amount of DCR-2 or commercially available CD300f antibodies, as shown on the x axis. Cells were then washed and stained with the test antibody (A) UP-D1 (B) UP-D2 (C) 234903 (D) rabbit CLM-1 and (E) goat LMIR3. The ability of the first antibody to block the second was calculated as a percentage binding, with 0% binding indicating full blocking (complete overlap of epitopes), and 100% binding indicating no blocking (no overlap of epitopes) (n=3).

The antibodies recognize distinct epitopes. We tested the ability of DCR-2 and the other antibodies of the CD300f panel to bind the CD300f Isoform 1 transfectants in the presence of other CD300f antibodies. UP-D1 showed 45% binding in the presence of UP-D2 or the gLMIR3 and 65% binding in the presence of 234903 (FIG. 5). Similarly, UP-D2 showed 30% binding in the presence of UP-D1 and 60-65% binding in the presence of 234903 or the gLMIR3. The 234903 mAb binding was significantly inhibited by DCR-2 and the gLMIR3, but not by either UP-D1 or UP-D2. The CLM-1 antibody did not block any antibodies, indicating none bind to an epitope within the amino acid residues 63-92. The gLMIR3 showed 70% and 50% binding in the presence of 234903 and UP-D1 respectively but UP-D2 mAb had no effect on its binding. The epitope recognized by the CLM-1 peptide antibody was further distinguished from the others as it was absent on immature myeloid cells and upregulated upon their maturation. DCR-2 did not prevent UP-D1 binding, thereby distinguishing the epitopes but it did prevent the 234903 mAb binding to full capacity indicating potential overlap in epitopes. Interestingly, rather than block binding of UP-D2, DCR-2 enhanced the binding of UP-D2 to CD300f (FIG. 5B).

Figure 6:
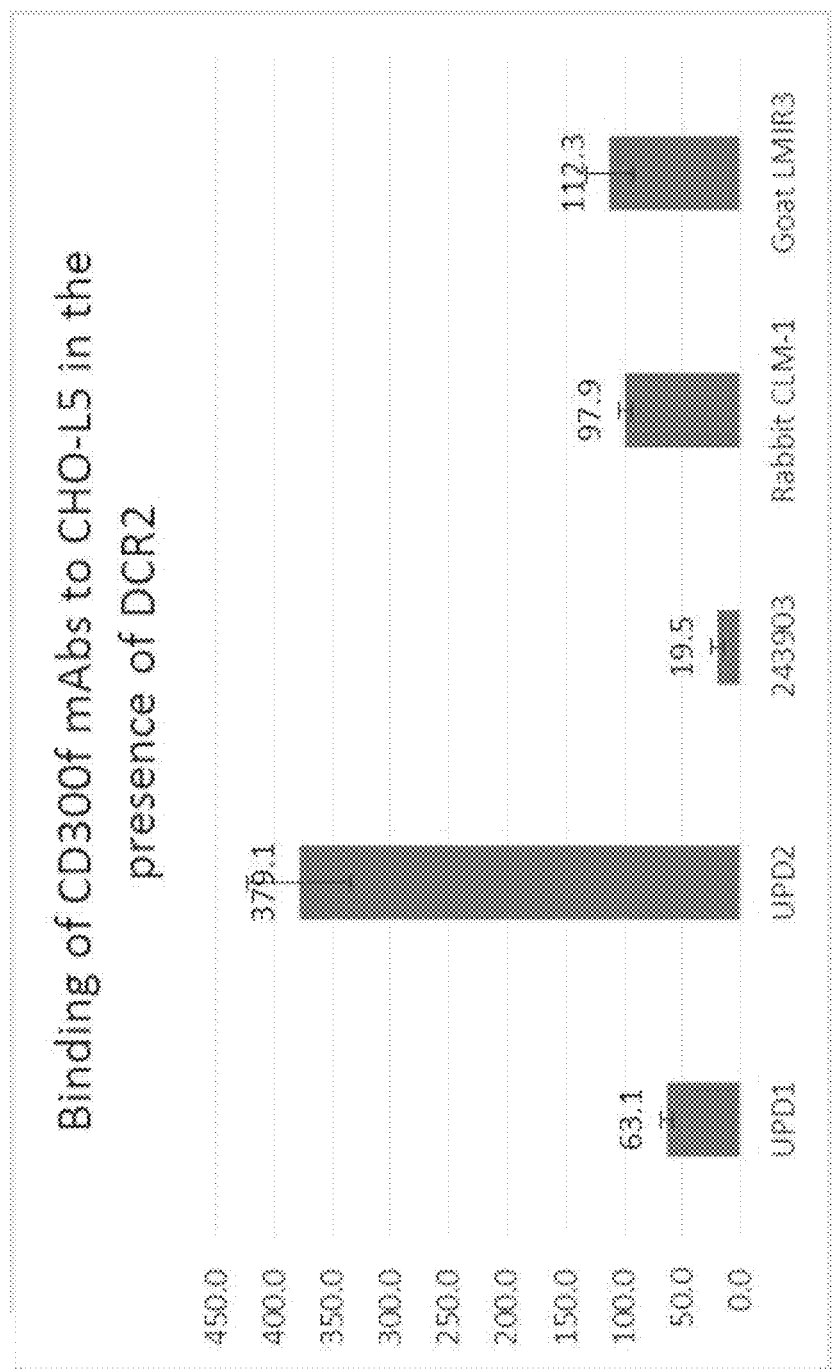
FIG. 6 is a graph showing binding of CD300f antibodies to CHO cells expressing CD300f (CHO-L5) in the presence of DCR-2.
Figure 7:
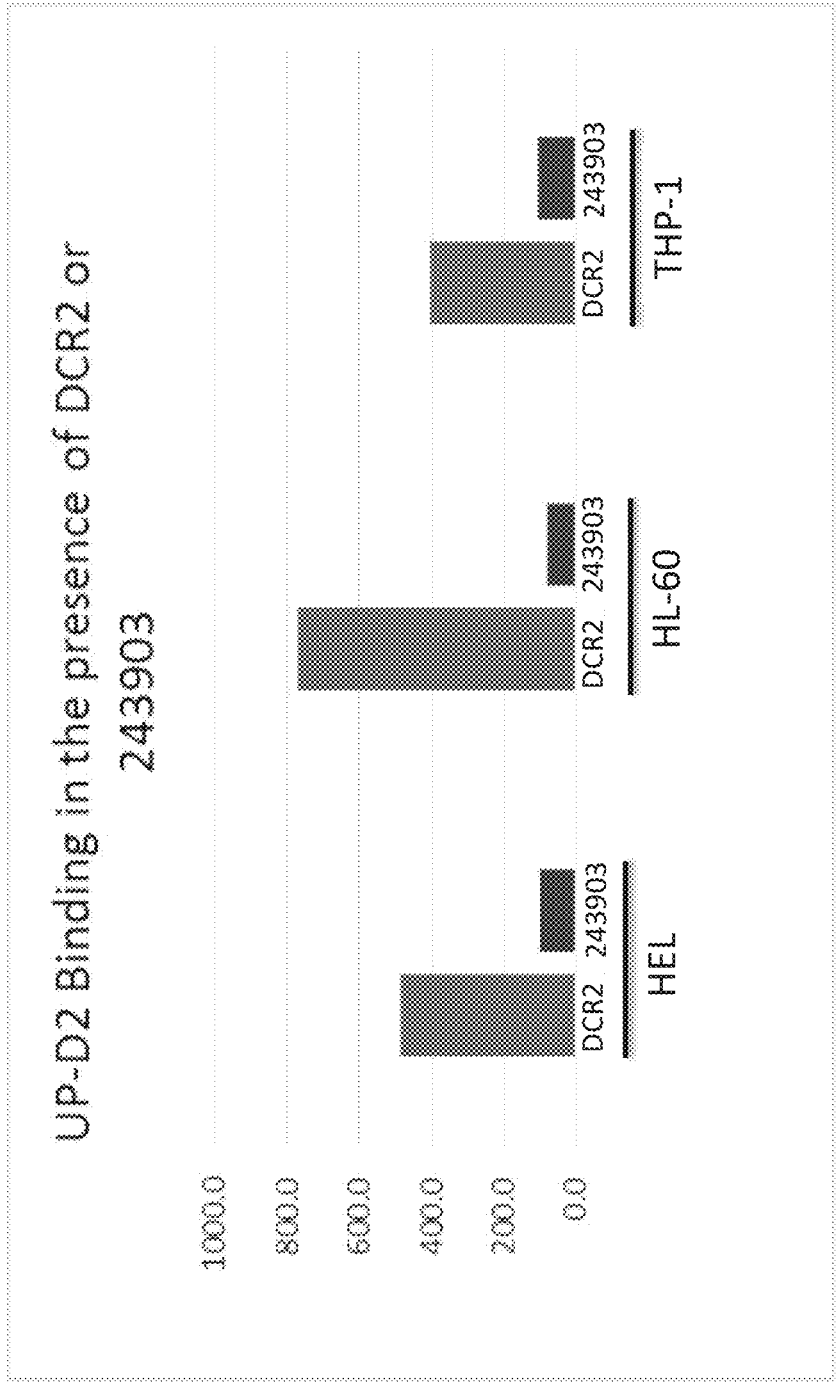
FIG. 7 is a graph showing binding of mAb UP-D2 to cell lines HEL, HL-60 and THP-1 in the presence of DCR-2 or 243903.

The ability of DCR-2 to enhance the binding of UP-D2 was further investigated. FIG. 6 shows the results of binding of CD300f antibodies to CHO cells expressing CD300f (CHO-L5) in the presence of DCR-2. As can be seen from FIG. 6, DCR-2 significantly enhances the binding of UP-D2. DCR-2 also enhanced the binding of UP-D2 to HEL, HL-60 and THP-1 cells when compared to the effect of mAb 342903 on UP-D2 binding to these cell lines (FIG. 7).

These results show that DCR-2 selectively enhances the binding of UP-D2 to CD300f expressed on cells.

Multiple CD300f RNA transcripts are expressed by myeloid derived cell lines. To identify the CD300f transcripts expressed in primary AMLs, we amplified and sequenced the complete coding region from healthy $CD14^+$ monocytes, several AML samples and myeloid derived cell line cDNA templates. Using an exon 1 specific primer (CD300f isoform 1 leader sequence), we amplified two sequences. One sequence has a short exon 4 of 20 amino acids ($CD300f^{S4}$) and was found in isoforms 1, 2, 3, 5 and 7. The second sequence had an alternatively spliced exon 4 that included an extra 14 amino acid residues ($CD300f^{L4}$) (STPAPTTPTSTTFT) and was found in isoforms 4 and 6. At least one isoform was amplified from each AML samples. This demonstrated that multiple forms of the CD300f extracellular component could be expressed together.

Figure 8:
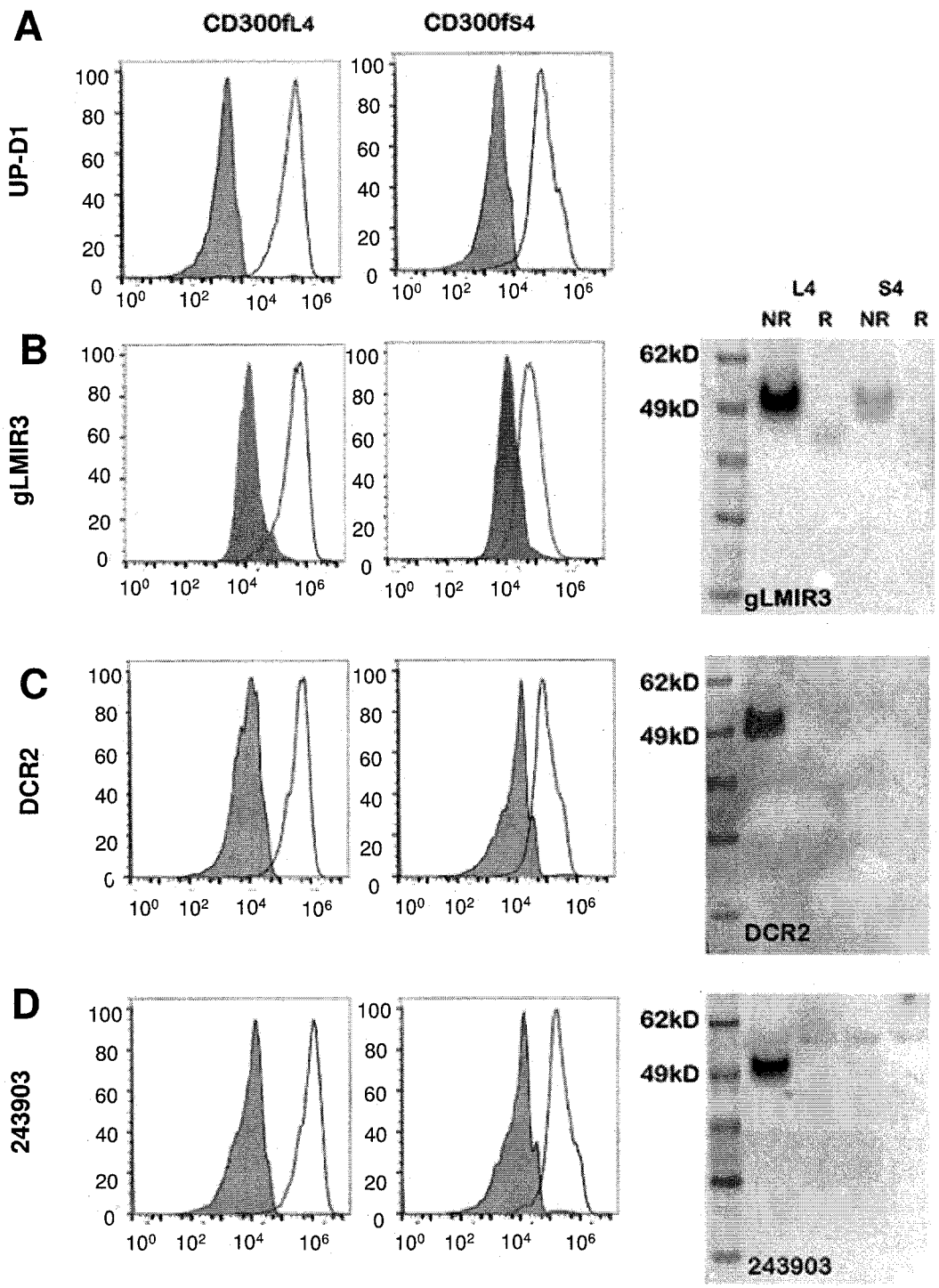
FIGS. 8A-8E are histograms (left) and western blots (right) showing the binding of CD300f antibodies to transfectants expressing the CD300f$^{L4}$ and CD300f$^{S4}$ extracellular isoforms. DCR-2 and commercially available CD300f antibodies were tested by flow cytometry for binding to CHO transfectants expressing isoforms of CD300f which include the amino acid sequence STPAPTTPTSTTFT (CD300f$^{L4}$) or exclude the amino acid sequence STPAPTTPTSTTFT (CD300f$^{S4}$). Each CD300f antibody (open histogram) was compared to appropriate isotype controls (Shaded histograms). Western blot analysis of CD300f protein in CD300f$^{L4}$ or CD300f$^{S4}$ lysates separated under non-reducing (NR) and reducing (R) conditions is shown on the right of the histograms.
In FIG. 8F, the CLM-1 peptide antibody was used to demonstrate that more CD300f protein was expressed by the CD300f$^{L4}$ transfectant than the CD300f$^{S4}$ transfectant but that, despite separating 5 fold more CD300f$^{S4}$ lysate than CD300f$^{L4}$ on the PAGE gel, the gLMIR3 only binds CD300f$^{L4}$. Similarly, DCR-2, 234903 and gLMIR3 were only able to bind to the non-reduced lysate from the CD300f$^{L4}$ transfectant whilst UP-D2 did not bind any protein by Western. Actin binding was used as a loading control. NR is non-reduced and N is reduced. Molecular weight markers are identified.
Figure 8:
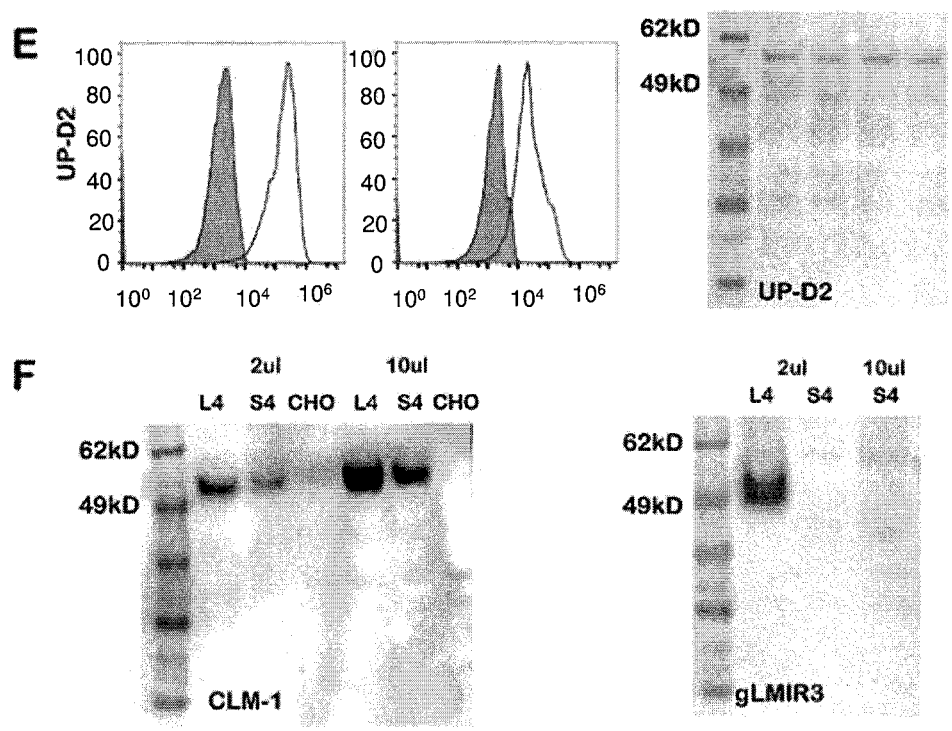

CD300f Isoforms are recognized by CD300f antibodies. We tested directly conjugated anti-CD300f antibodies for binding to $CD300f^{L4}$ and $CD300f^{S4}$ extracellular region expressed in CHO cells and found that they all bound to the $CD300^{S4}$ and $CD300f^{L4}$ extracellular region of CD300f when expressed in CHO cells (FIG. 8). Comparing the MFI ratios of UP-D1 to each, revealed that UP-D1 bound to $CD300f^{L4}$ with a 3 fold higher ratio compared to $CD300f^{S4}$ whereas there was less than 2 fold difference in UP-D2, 234903 and DCR-2 binding to $CD300f^{L4}$ compared to $CD300f^{S4}$. This suggested that the UP-D1 mAb bound to a distinct epitope on CD300f. Western blot analysis showed that 234903, DCR-2 mAb and the gLMIR3 antibody bound to a 49 kD protein from the $CD300f^{L4}$ under non-reducing conditions. In reducing conditions, the binding was markedly diminished. These results indicate the disulphide bonds determining the tertiary structure of CD300f influence the antibody binding epitopes. In contrast, there was little binding to the $CD300f^{S4}$ form in either reducing or non-reducing conditions, even when 10 fold levels of protein were analysed. The CLM-1 antibody was used to confirm CD300f expression in transfectants could not account for the absence or very weak binding of mAbs to the $CD300f^{S4}$ protein.

The kinetics of binding of DCR-2 to CD300f-Fc recombinant protein was determined using Bio-Layer Interferometry analysis on a BLItz System (Fortebio, Pall Life Sciences). The results are shown in FIG. 9.

Figure 10:
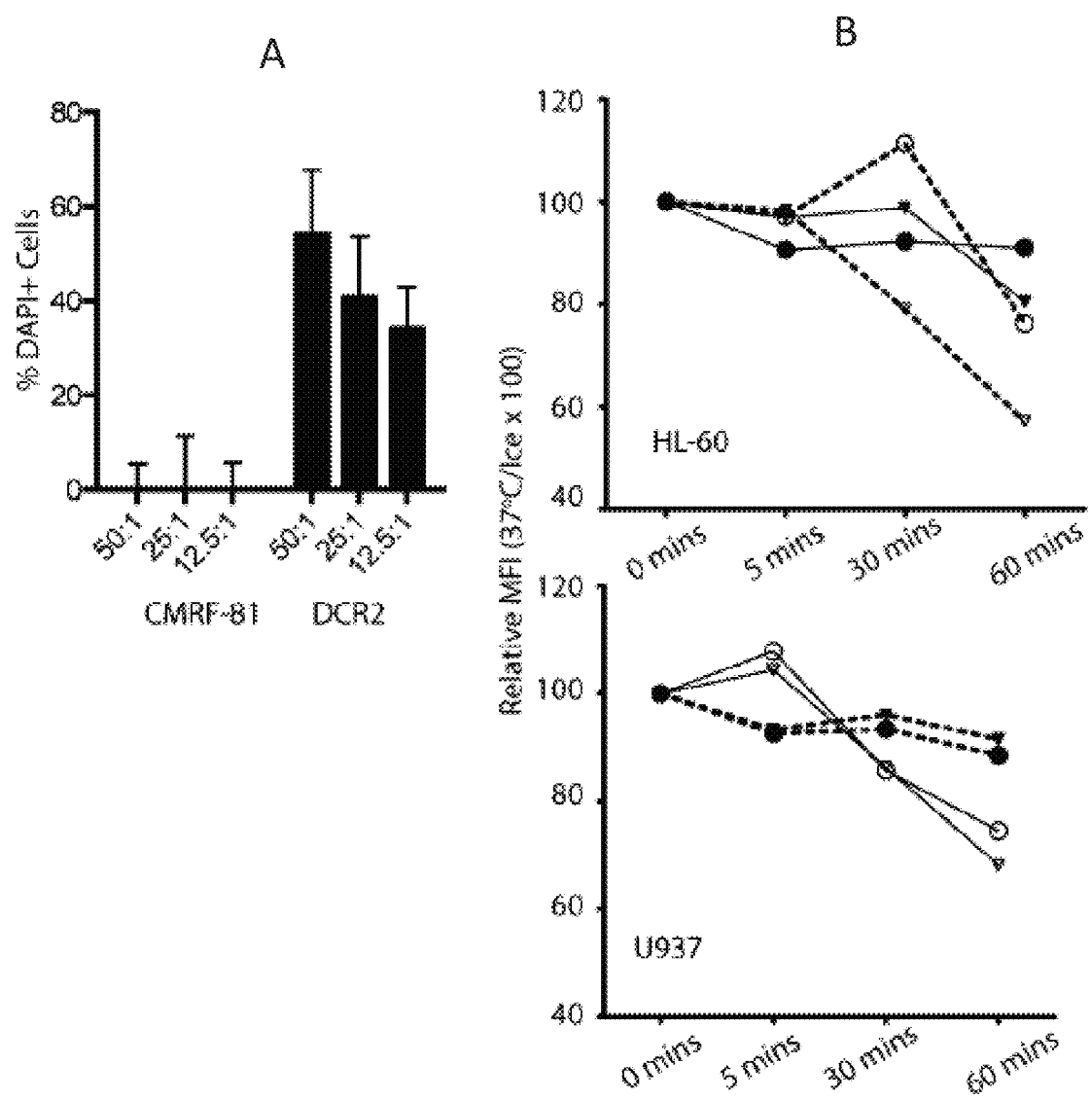
FIG. 10A is a graph showing antibody-dependent cell-mediated cytotoxicity (ADCC) of HL-60 cells caused by DCR-2 compared to an isotype control (CMRF-81).
FIG. 10B are graphs showing internalisation of the UP-D1 and DCR-2 mAbs at 37° C. from the surface of U937 and HL-60 which was detected by monitoring the directly labelled antibodies (Total) over time compared with remaining surface Ig detected by anti-mouse AF647 (surface). Triangles represent DCR-2 and circles represent UP-D1. Solid lines and closed symbols represent total staining and dashed lines and open symbols represent surface staining.
Figure 11:
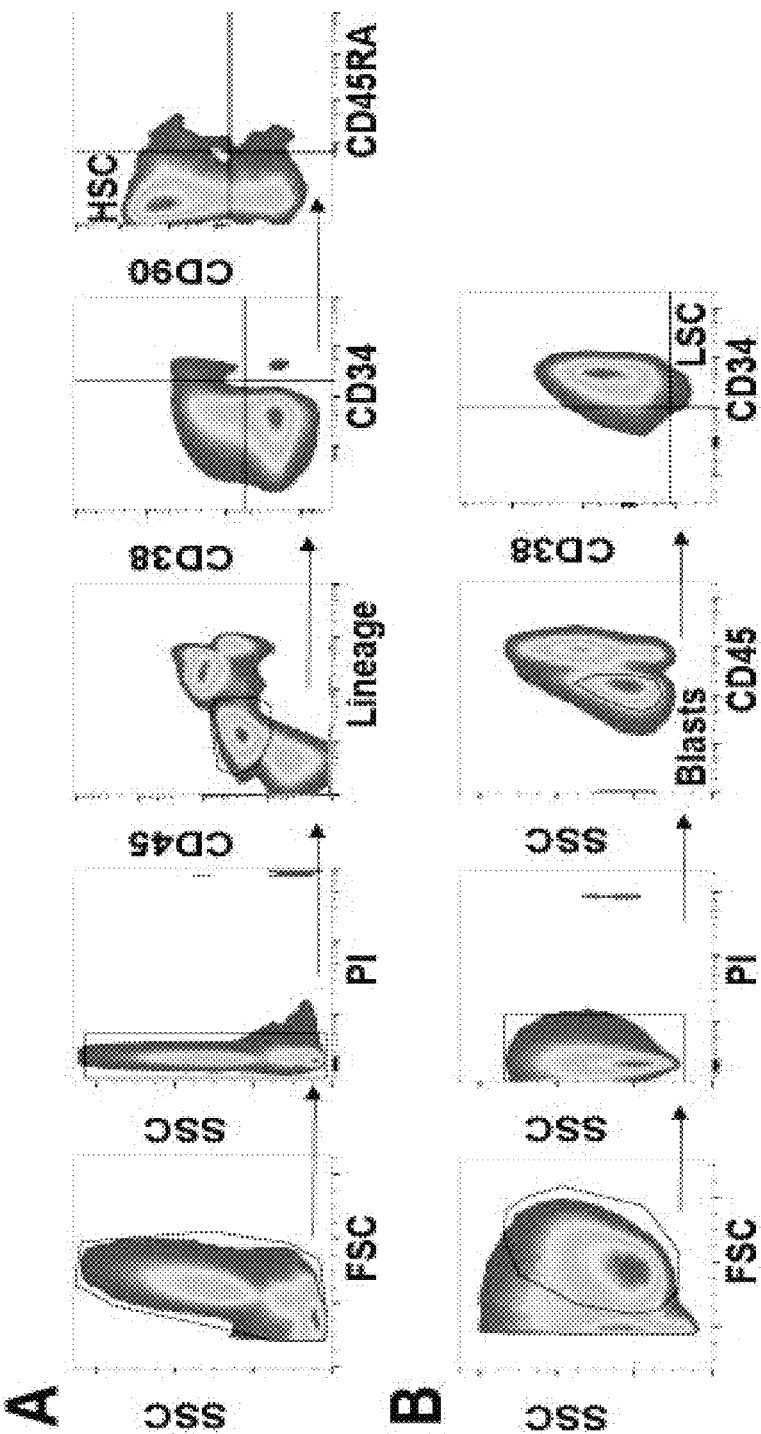
FIG. 11 shows the gating strategy to identify blasts, LSCs and HSCs. (A) After initially gating on PI negative viable cells, hematopoietic stem cells were identified as lineage-CD45dimCD34+CD38-CD45RA-CD90+. (B) Blasts were identified as CD45dimSSClow. The leukemia stem cell enriched CD34+CD38− fraction was identified from this gate.

Antibodies to CD300f mediate ADCC and are internalized along with CD300f. DCR-2 was effective in antibody-dependent cell-mediated cytotoxicity (ADCC) of the HL-60 cell line by IL-2 activated mouse splenocytes (FIG. 10A). Additionally, after 30 minutes at 37° C., 40% of DCR-2 and 25% of UP-D1 had internalized from the surface of HL-60 or U937 when assessed by flow cytometry (FIGS. 10B and 10C). UP-D2 was found to have a low affinity for CD300f resulting in loss of binding rather than internalization. Confocal microscopy confirmed CD300f antibody was internalized from the surface membrane of HL-60 and U937, healthy $CD14^+$ monocytes and AML blasts following incubation at 37° C. (FIGS. 10B and 10C). Little surface CD300f remained at this time, indicating that most CD300f bound antibody internalized, regardless of the surface form of CD300f bound.

DCR-2 Sequence

The heavy chain variable region and the light chain variable region of DCR-2 was sequenced. SEQ ID NO: 1 represents the amino acid sequence of the DCR-2 heavy chain variable region. SEQ ID NO: 5 represents the amino acid sequence of the DCR-2 light chain variable region.

The DCR-2 heavy chain joining region has the sequence GQGTLVTV.

The DCR-2 light chain sequence which overlaps with the constant region has the sequence TKLEIKR.

Humanization of the $V_H$ Region of DCR2

The amino acid sequence of the $V_H$ region of mouse DCR-2 was aligned with human $V_H$ sequence to identify the amino acids in the framework region that differed between mouse and human, in order to identify amino acids to be changed to humanize the mouse DCR-2 sequence. An alignment of the mouse (top, A) and proposed humanised (bottom, B) $V_H$ regions of DCR-2 are shown in FIG. 12. The top sequence shows the mouse DCR-2 $V_H$ amino acid sequence, and the bottom sequence shows the proposed humanized DCR-2 $V_H$ amino acid sequence. The amino acid residues to be changed to the human sequence are in bold and underlined. The CDR sequences of mouse DCR-2 are boxed.

Discussion

The development of new antibody based therapeutics is limited by the availability of appropriate antibodies that target cell surface protein targets. CD300f was identified as a member of the CD300 gene family, and we have showed that CD300f is expressed on AML blasts and in the $CD34^+$ $CD38^-$ LSC enriched fraction. We have produced a monoclonal antibody, DCR-2.

mAb DCR-2 targets CD300f with high affinity. DCR-2 mediates antibody dependent cell mediated cytotoxicity. DCR-2 also enhances the binding of UP-D2 to CD300f. The inventors envisage that DCR-2 will be useful for the treatment of myeloid leukaemias, such as AML.

The invention claimed is:

1. An isolated antibody, or antigen binding fragment thereof, which specifically binds to an extracellular domain of CD300f, wherein the antibody, or antigen binding fragment thereof, comprises; (a) a heavy chain variable region comprising a complementarity determining region 1 (CDR1) that comprises the amino acid sequence of SEQ ID NO: 2, a complementarity determining region 2 (CDR2) that comprises the amino acid sequence of SEQ ID NO: 3, and a complementarity determining region 3 (CDR3) that comprises the amino acid sequence of SEQ ID NO: 4; and (b) a light chain variable region comprising a complementarity determining region 1 (CDR1) that comprises the amino acid sequence of SEQ ID NO: 6, a complementarity determining region 2 (CDR2) that comprises the amino acid sequence of SEQ ID NO: 7, and a complementarity determining region 3 (CDR3) that comprises the amino acid sequence of SEQ ID NO: 8.

2. The antibody, or antigen binding fragment thereof, of claim 1, wherein the heavy chain variable region comprises an amino acid sequence that is at least 70% identical to the amino acid sequence of SEQ ID NO: 1, and comprises a CDR1 comprising the amino acid sequence of SEQ ID NO: 2, a CDR2 comprising the amino acid sequence of SEQ ID NO: 3, and a CDR3 comprising the amino acid sequence of SEQ ID NO: 4.

3. The antibody, or antigen binding fragment thereof, of claim 1, wherein the light chain variable region comprises an amino acid sequence that is at least 70% identical to the amino acid sequence of SEQ ID NO: 5, and comprises a CDR1 comprising the amino acid sequence of SEQ ID NO: 6, a CDR2 comprising the amino acid sequence of SEQ ID NO: 7, and a CDR3 comprising the amino acid sequence of SEQ ID NO: 8.

4. The antibody, or antigen binding fragment thereof, of claim 1, wherein the heavy chain variable region comprises the amino acid sequence of SEQ ID NO: 1.

5. The antibody, or antigen binding fragment thereof, of claim 1, wherein the light chain variable region comprises the amino acid sequence of SEQ ID NO: 5.

6. The antibody, or antigen binding fragment thereof, of claim 1, wherein the heavy chain comprises the amino acid sequence of SEQ ID NO: 13.

7. The antibody, or antigen binding fragment thereof, of claim 1, wherein the light chain comprises the amino acid sequence of SEQ ID NO: 14.

8. The antibody of claim 1, wherein the antibody, or antigen binding fragment thereof, is selected from the group consisting of F(ab')2, Fab', Fab, Fv, sFv, scFv, bispecific antibody or BiTE.

9. An immunoconjugate comprising the antibody, or antigen binding fragment thereof, of claim 1, coupled to a moiety.

10. The immunoconjugate of claim 9, wherein the moiety is a therapeutic moiety.

11. The immunoconjugate of claim 10, wherein the therapeutic moiety is selected from the group consisting of cytotoxic agent; pro-apoptotic agent; radioisotope; and immunotoxin.

12. A pharmaceutical composition comprising the antibody, or antigen binding fragment thereof, of claim 1.

13. A pharmaceutical composition comprising the immunoconjugate of claim 9.

* * * * *